(12) United States Patent
Gerlach et al.

(10) Patent No.: US 7,807,693 B2
(45) Date of Patent: Oct. 5, 2010

(54) SUBSTITUTED PROLINAMIDES, MANUFACTURING, AND THE USE THEREOF AS MEDICAMENTS

(75) Inventors: Kai Gerlach, Biberach (DE); Georg Dahmann, Attenweiler (DE); Herbert Nar, Ochsenhausen (DE); Roland Pfau, Biberach (DE); Henning Priepke, Warthausen (DE); Annette Schuler-Metz, Ulm (DE); Wolfgang Wienen, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/749,204

(22) Filed: May 16, 2007

(65) Prior Publication Data

US 2008/0139605 A1    Jun. 12, 2008

(30) Foreign Application Priority Data

May 16, 2006  (EP) ................. 06113977
Feb. 16, 2007  (EP) ................. 07102566

(51) Int. Cl.
- A61K 31/4725 (2006.01)
- A61K 31/4025 (2006.01)
- C07D 217/00 (2006.01)
- C07D 217/06 (2006.01)
- C07D 207/08 (2006.01)
- C07D 207/12 (2006.01)

(52) U.S. Cl. ............. 514/311; 514/314; 514/422; 546/159; 546/162; 546/165; 548/518

(58) Field of Classification Search ........... 514/311, 514/314, 422; 546/159, 152, 165; 548/518
See application file for complete search history.

(56) References Cited

U.S. PATENT DOCUMENTS

2007/0015812 A1   1/2007  Boehringer et al.

FOREIGN PATENT DOCUMENTS

| CA | 2 520 893 A1 | 10/2004 |
|---|---|---|
| CA | 2 521 069 A1 | 10/2004 |
| CA | 2 529 453 A1 | 12/2004 |
| CA | 2 549 589 A1 | 6/2005 |
| CA | 2 561 057 A1 | 10/2005 |
| CA | 2 581 172 A1 | 3/2006 |
| WO | 03/045912 A1 | 6/2003 |
| WO | 2004/087646 A2 | 10/2004 |
| WO | 2004/087695 A1 | 10/2004 |
| WO | 2004/110433 A1 | 12/2004 |
| WO | WO 2004110433 A1 * | 12/2004 |
| WO | 2005/058817 A1 | 6/2005 |
| WO | 2005/092849 A1 | 10/2005 |
| WO | 2006/032342 A2 | 3/2006 |
| WO | 2006/108709 A1 | 10/2006 |

OTHER PUBLICATIONS

George J. Qualich, et al; Synthesis of 1,2,3,4-Thetrahydroisoquinolines Containing Electron-Withdrawing Groups; Journal of Organic Chemistry (1998) vol. 63 pp. 4116-4119.
Molina Mhatre, et al; Thrombin, a Mediator of Neurotoxicity and Memory Impairment; Neurobiology of Aging (2004) vol. 25 pp. 783-793.
Haruhiko Akiyama, et al; Thrombin Accumulation in Brain of Patients with Alzheimer's Disease; Neuroscience Letters (1992) vol. 146 pp. 152-154.
Sang-H. Choi, et al; Thrombin-Induced Microglial Activation Produces Degeneration of Nigral Dopaminergic Neurons in Vivo; The Journal of Neuroscience (2003) vol. 23 No. 13 pp. 5877-5886.
International Search Report for PCT/EP2007/054631 mailed Nov. 14, 2007.
Jag P. Heer et al; Preparation of 1,7-Disubstituted-1,2,3,4-Tetrahydroisoquinolines; Synthetic Communications (2002) vol. 32 No. 16 pp. 2555-2563.
John D. Harling, et al; A Facile Synthesis of the 3-Amino-5,6,7,8-Tetrahydro[1,6]Naphthyridine System and Some Alkylated and Polycyclic Homologues; Synthetic Communications (2001) vol. 31 No. 5 pp. 787-797.
Simone Durand-Henchoz, et al; No. 585.—Nitration of 2-Methyl-1,2,3,4-Tetrahydroisoquinoline; Bulletin of the French Chemical Society (1966) vol. 11, pp. 3413-3416.

* cited by examiner

*Primary Examiner*—Yong Chu
(74) *Attorney, Agent, or Firm*—Michael P. Morris; Usha R. Patel; Edouard G. Lebel

(57) ABSTRACT

The present invention relates to new substituted prolinamides of general formula (I)

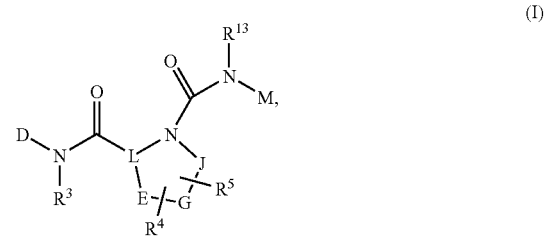

wherein D, L, E, G, J, M, $R^3$, $R^4$, $R^5$ and $R^{13}$ are defined as in the specification, the tautomers, the enantiomers, the diastereomers, the mixtures, and the salts thereof.

15 Claims, No Drawings

SUBSTITUTED PROLINAMIDES, MANUFACTURING, AND THE USE THEREOF AS MEDICAMENTS

BACKGROUND OF THE INVENTION

This application claims priority of EP 06113977, filed May 16, 2006, and EP 07102566, filed Feb. 16, 2007, both of which are incorporated in their entirety herein by reference.

The present invention relates to new substituted prolinamides of general formula (I)

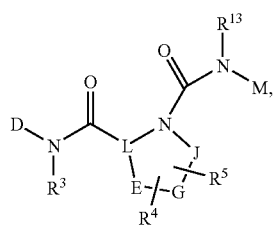

(I)

the tautomers, the enantiomers, the diastereomers, the mixtures and the salts thereof, particularly the physiologically acceptable salts thereof with inorganic or organic acids or bases, which have valuable properties.

The compounds of the above general formula (I) as well as the tautomers, the enantiomers, the diastereomers, the mixtures and the salts thereof, particularly the physiologically acceptable salts thereof with inorganic or organic acids or bases, and the stereoisomers thereof, have valuable pharmacological properties, particularly an antithrombotic activity and a factor Xa-inhibiting activity.

SUMMARY OF THE INVENTION

The present application relates to new compounds of the above general formula (I), the preparation thereof, the pharmaceutical compositions containing the pharmacologically effective compounds, the preparation and use thereof.

DETAILED DESCRIPTION OF THE INVENTION

A 1st embodiment of the present invention encompasses those compounds of general formula (I), wherein
D denotes a substituted bicyclic ring system of formula

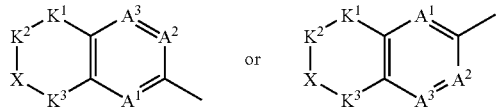

wherein
$K^1$
  denotes a bond, or an —$CH_2$—, —$CHR^{7a}$—, —$CR^{7b}R^{7c}$ or —C(O) group, and wherein
  $R^{7a}/R^{7b}/R^{7c}$
    each independently of one another denote a fluorine atom, a hydroxy, $C_{1-5}$-alkyloxy, amino, $C_{1-5}$-alkylamino, di-($C_{1-5}$-alkyl)-amino, $C_{3-5}$-cycloalkyleneimino, $C_{1-5}$-alkylcarbonylamino group, a $C_{1-5}$-alkyl group which may be substituted by 1-3 fluorine atoms, a hydroxy-$C_{1-5}$-alkyl, $C_{1-5}$-alky-loxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group,
      while the two groups $R^{7b}/R^{7c}$ may not simultaneously be bound to the cyclic carbon atom via a heteroatom, except where —$C(R^{7b}R^{7c})$— corresponds to a —$CF_2$ group, or
    $R^{7a}$ denotes a fluoro-, chloro-, bromo-, methyl-, methoxy-, amino- or nitro-substituted phenyl or monocyclic heteroaryl group, or
    two groups $R^{7b}/R^{7c}$ together with the cyclic carbon atom may form a 3-, 4-, 5-, 6- or 7-membered saturated carbocyclic group or a cyclopentene, cyclohexene, oxetan, azetidine, thietan, tetrahydrofuran, pyrrolidine, tetrahydrothiophene, tetrahydropyran, piperidine, pentamethylene sulphide, hexamethyleneimine, 1,3-dioxolan, 1,4-dioxane, hexahydropyridazine, piperazine, thiomorpholine, morpholine, 2-imidazolidinone, 2-oxazolidinone, tetrahydro-2(1H)-pyrimidinone or [1.3]oxazinan-2-one ring,
      while the methylene groups thereof may be substituted by 1-2 $C_{1-3}$-alkyl or $CF_3$— groups, and/or
      the methylene groups thereof, if they are not bound to a heteroatom, may be substituted by 1-2 fluorine atoms, and/or wherein a —$CH_2$ group besides an N atom may be replaced by a —CO group, and/or
      the imino groups of which may each be substituted by a $C_{1-3}$-alkyl or $C_{1-3}$-alkylcarbonyl group, and/or
      wherein the sulphur atom may be oxidised to form a sulphoxide or sulphone group,
$K^2$ and $K^3$
  each independently of one another denote a —$CH_2$, —$CHR^{8a}$, —$CR^{8b}R^{8c}$ or a —C(O) group, wherein $R^{8a}/R^{8b}/R^{8c}$
    each independently of one another denote a $C_{1-5}$-alkyl group which may be substituted by 1-3 fluorine atoms, a hydroxy-$C_{1-5}$-alkyl, $C_{1-5}$-alkyloxy-$C_{1-5}$-alkyl, amino-$C_{1-5}$-alkyl, $C_{1-5}$-alkylamino-$C_{1-5}$-alkyl, di-($C_{1-5}$-alkyl)-amino-$C_{1-5}$-alkyl, $C_{4-7}$-cycloalkyleneimino-$C_{1-5}$-alkyl, carboxy-$C_{0-5}$-alkyl, $C_{1-5}$-alkyloxycarbonyl-$C_{0-5}$-alkyl, aminocarbonyl-$C_{0-5}$-alkyl, $C_{1-5}$-alkylaminocarbonyl-$C_{0-5}$-alkyl, di-($C_{1-5}$-alkyl)-aminocarbonyl-$C_{0-5}$-alkyl or a $C_{4-7}$-cycloalkyleneiminocarbonyl-$C_{0-5}$-alkyl group,
    or two groups $R^{8b}/R^{8c}$ together with the cyclic carbon atom may form a 3-, 4-, 5-, 6- or 7-membered saturated carbocyclic group or a cyclopentene, cyclohexene, oxetan, azetidine, thietan, tetrahydrofuran, pyrrolidine, tetrahydrothiophene, tetrahydropyran, piperidine, pentamethylene sulphide, hexamethyleneimine, hexahydropyridazine, tetrahydro-2(1H)-pyrimidinone, [1.3]oxazinan-2-one ring,
      while the methylene groups thereof may be substituted by 1-2 $C_{1-3}$-alkyl or $CF_3$— groups, and/or
      the methylene groups thereof, if they are not bound to a heteroatom, may be substituted by 1-2 fluorine atoms, and/or wherein a —CH$_2$ group besides a nitrogen atom may be replaced by a —CO group, and/or the imino groups of which may each be substituted by a C$_{1-3}$-alkyl or C$_{1-3}$-alkylcarbonyl group, and/or wherein the sulphur atom may be oxidised to form a sulphoxide or sulphone group, with the proviso that a heteroatom introduced by R$^{8b}$ or R$^{8c}$ must not be only one carbon atom away from X in formula (I), and in all not more than four groups selected from among R$^{7a}$, R$^{7b}$, R$^{7c}$, R$^{8a}$, R$^{8b}$ and R$^{8c}$ may be present, and X denotes an oxygen or sulphur atom, a CF$_2$, sulphene, sulphone or a NR$^1$ group, wherein R$^1$ denotes a hydrogen atom or a hydroxy, C$_{1-3}$-alkyloxy, amino, C$_{1-3}$-alkylamino, di-(C$_{1-3}$-alkyl)-amino, a C$_{1-5}$-alkyl, C$_{2-5}$-alkenyl-CH$_2$, C$_{2-5}$-alkynyl-CH$_2$, C$_{3-6}$-cycloalkyl, C$_{4-6}$-cycloalkenyl, oxetan-3-yl, tetrahydrofuran-3-yl, benzyl, C$_{1-5}$-alkyl-carbonyl, trifluoromethylcarbonyl, C$_{3-6}$-cycloalkyl-carbonyl, C$_{1-5}$-alkyl-sulphonyl, C$_{3-6}$-cycloalkyl-sulphonyl, aminocarbonyl, C$_{1-5}$-alkylaminocarbonyl, di-(C$_{1-5}$-alkyl)-aminocarbonyl, C$_{1-5}$-alkyloxycarbonyl, C$_{4-7}$-cycloalkyleneiminocarbonyl group, while the methylene and methyl groups present in the groups mentioned above may additionally be substituted by a C$_{1-3}$alkyl, carboxy, C$_{1-5}$-alkoxycarbonyl group, or may be substituted by a hydroxy, C$_{1-5}$-alkyloxy, amino, C$_{1-5}$-alkylamino, C$_{1-5}$-dialkylamino or C$_{4-7}$-cycloalkyleneimino group, if the methylene or methyl groups are not directly bound to a heteroatom selected from among O, N or S, and/or one to three hydrogen atoms may be replaced by fluorine atoms, if the methylene or methyl groups are not directly bound to a heteroatom selected from among O, N or S, and wherein A$^1$ denotes either N or CR$^{10}$, A$^2$ denotes either N or CR$^{11}$, A$^3$ denotes either N or CR$^{12}$, while R$^{10}$, R$^{11}$ and R$^{12}$ each independently of one another denote a hydrogen, fluorine, chlorine, bromine or iodine atom, or a C$_{1-5}$-alkyl, CF$_3$, C$_{2-5}$-alkenyl, C$_{2-5}$-alkynyl, a cyano, carboxy, C$_{1-5}$-alkyloxycarbonyl, hydroxy, C$_{1-3}$-alkyloxy, CF$_3$O, CHF$_2$O, CH$_2$FO, amino, C$_{1-5}$-alkylamino, di-(C$_{1-5}$-alkyl)-amino or C$_{4-7}$-cycloalkyleneimino group, and -L-E-G-J- denotes a —C—C—C—C or —C—C=C—C group which may be substituted by R$^4$ and R$^5$, and R$^3$ denotes a hydrogen atom or a C$_{1-3}$-alkyl group, and R$^4$ denotes a hydrogen atom or a straight-chain or branched C$_{1-6}$-alkyl, C$_{2-6}$-alkenyl or C$_{2-6}$-alkynyl group, wherein the hydrogen atoms of the methylene and/or methyl fragments of the straight-chain or branched C$_{1-6}$-alkyl, C$_{2-6}$-alkenyl or C$_{2-6}$-alkynyl group may optionally be wholly or partly replaced by fluorine atoms, and/or wherein the hydrogen atoms of the methylene and/or methyl fragments of the straight-chain or branched C$_{1-6}$-alkyl, C$_{2-6}$-alkenyl or C$_{2-6}$-alkynyl group may optionally each be substituted independently of one another by one to two substituents selected from among a C$_{3-5}$-cycloalkyl group, a nitrile, hydroxy or C$_{1-5}$-alkyloxy group, while the hydrogen atoms of the C$_{1-5}$-alkyloxy group may optionally be wholly or partly replaced by fluorine atoms, an allyloxy, propargyloxy, benzyloxy, C$_{1-5}$-alkylcarbonyloxy, C$_{1-5}$-alkyloxycarbonyloxy, carboxy-C$_{1-5}$-alkyloxy, C$_{1-5}$-alkyloxycarbonyl-C$_{1-5}$-alkyloxy, mercapto, C$_{1-5}$-alkylsulphanyl, C$_{1-5}$-alkylsulphinyl, C$_{1-5}$-alkylsulphonyl, carboxy, C$_{1-5}$-alkyloxycarbonyl, aminocarbonyl, C$_{1-5}$-alkylaminocarbonyl, di-(C$_{1-5}$-alkyl)-aminocarbonyl, C$_{4-7}$-cycloalkyleneiminocarbonyl, aminosulphonyl, C$_{1-5}$-alkylaminosulphonyl, di-(C$_{1-5}$-alkyl)-aminosulphonyl, C$_{4-7}$-cycloalkyleneiminosulphonyl, amino, C$_{1-5}$-alkylamino, di-(C$_{1-5}$-alkyl)-amino, C$_{1-5}$-alkylcarbonylamino, C$_{1-5}$-alkylsulphonylamino, N—(C$_{1-5}$-alkylsulphonyl)-C$_{1-5}$-alkylamino, C$_{3-6}$-cycloalkylcarbonylamino group, or a morpholinyl, thiomorpholinyl, pyrrolidinyl, piperidinyl, piperazinyl, tetrahydrofuranyl, tetrahydropyranyl group, while the above-mentioned carbocyclic and heterocyclic groups in the ring may each be substituted by 1-4 C$_{1-3}$-alkyl or C$_{1-3}$-alkylcarbonyl groups or by 1-2 oxo groups, and/or wherein the hydrogen atoms of the sp$^2$-hybridised carbon atoms of the straight-chain or branched C$_{2-6}$-alkenyl group may optionally be wholly or partly replaced by fluorine atoms, or a nitrile, carboxy, aminocarbonyl, C$_{1-5}$-alkylaminocarbonyl, C$_{3-6}$-cycloalkylamino-carbonyl, di-(C$_{1-5}$-alkyl)-aminocarbonyl, C$_{1-5}$-alkyloxycarbonyl or a C$_{4-7}$-cycloalkyleneiminocarbonyl group wherein optionally a methylene group may be replaced by a oxygen, sulphur or C$_{0-3}$-alkyl-substituted nitrogen atom, or a phenyl, mono- or bicyclic heteroaryl, phenyl-C$_{1-5}$-alkyl or mono- or bicyclic heteroaryl-C$_{1-5}$-alkyl group, which may optionally be mono- to trisubstituted in the phenyl or heteroaryl moiety by identical or different substituents selected from among fluorine, chlorine, bromine and iodine atoms, and C$_{1-5}$-alkyl, trifluoromethyl, amino, C$_{1-5}$-alkyl-amino, di-(C$_{1-5}$-alkyl)-amino, hydroxy, C$_{1-5}$-alkyloxy, mono-, di- or trifluoromethoxy, carboxy and C$_{1-5}$-alkyloxycarbonyl group, and if -L-E-G-J- denotes a —C—C—C—C group, R$^4$ at E or G may also denote a fluorine atom or a hydroxy, methoxy, C$_{3-5}$-alkenyl-oxy, C$_{3-5}$-alkynyloxy, C$_{2-5}$-alkyloxy, C$_{3-6}$-cycloalkyl-oxy, C$_{1-5}$-alkylaminocarbonyloxy, di(C$_{1-5}$-alkyl)aminocarbonyloxy or C$_{4-7}$-cycloalkyleneiminocarbonyloxy, phenyl-C$_{0-3}$-alkyloxy, heteroaryl-C$_{0-3}$-alkyloxy, amino, C$_{1-5}$-alkylamino, di-(C$_{1-5}$-alkyl)-amino, C$_{4-7}$-cycloalkyleneimino, C$_{1-3}$-acylamino, (C$_{1-3}$-acyl) C$_{1-3}$-alkylamino, C$_{1-5}$-alkyloxycarbonylamino, C$_{1-5}$-alkylaminocarbonylamino, di(C$_{1-5}$-alkyl)aminocarbonylamino or a C$_{4-7}$-cycloalkyleneiminocarbonylamino group, while the methyl or methylene groups present in the above-mentioned alkyl or cycloalkyl groups may each independently of one another be substituted by a substituent selected from among morpholinyl, thiomorpholinyl, pyrrolidinyl, piperidinyl, piperazinyl, tetrahydrofuranyl, tetrahydropyranyl, dimethylaminocarbonyl, C$_{1-5}$-alkyloxycarbonyl, carboxy, methyl, hydroxy, methoxy or amino, and the above-mentioned phenyl or heteroaryl groups may optionally be mono- to trisubstituted by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy- and $C_{1-5}$-alkyloxycarbonyl group, with the proviso
that two heteroatoms selected from among oxygen and nitrogen are separated from one another by precisely one optionally substituted $CH_2$ group, and/or
that two atoms form an —O—O or —S—O— bond,
is excluded, and $R^5$ denotes a hydrogen atom, a $C_{1-5}$ alkyl, $C_{2-5}$ alkenyl or $C_{2-5}$ alkynyl or a phenyl-$C_{0-5}$-alkyl group, wherein the alkyl group may be substituted by a hydroxy, methoxy, hydroxycarbonyl or $C_{1-5}$-alkoxycarbonyl group,
or if $R^5$ is linked to E or G it may also denote a hydroxy or methoxy group, or $R^4$ and $R^5$ if they are bound to the same carbon atom, they may form together with the carbon atom a —C=O group or a —CF$_2$— group, or $R^4$ and $R^5$ if they are bound to the same carbon atom or to two adjacent carbon atoms, together with the carbon atom(s) they may form a 3-7-membered carbocyclic group or a monounsaturated 5-7 membered carbocyclic group,
wherein one of the carbon chain members of this cyclic group may be replaced by an oxygen or sulphur atom or a —NH, —N($C_{1-5}$-alkyl), —N($C_{1-4}$-alkylcarbonyl) or a carbonyl, sulphinyl or sulphonyl group, and/or
two directly adjacent carbon chain members of these $C_{4-7}$-carbocyclic groups may together be replaced by a —C(O)NH, —C(O)N($C_{1-5}$-alkyl), —S(O)$_2$NH, or —S(O)$_2$N($C_{1-5}$-alkyl) group, and/or
four directly adjacent carbon chain members of these $C_{5-7}$-carbocyclic groups may together be replaced by an —O—CH$_2$—CH$_2$—O group, and/or
1 to 3 carbon atoms of these 3-7-membered cyclic groups may optionally be substituted independently of one another by in each case one or two fluorine atoms or one or two $C_{1-5}$-alkyl groups or a hydroxy, formyloxy, $C_{1-5}$-alkyloxy, $C_{1-5}$-alkylcarbonyloxy, amino, $C_{1-5}$-alkylamino, di-($C_{1-5}$-alkyl)-amino, $C_{4-7}$-cycloalkyleneimino, $C_{1-5}$-alkylcarbonylamino, $C_{3-6}$-cycloalkylcarbonylamino, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group,
with the proviso that a cyclic group of this kind formed from $R^4$ and $R^5$ together,
wherein two nitrogen atoms or one nitrogen and one oxygen atom in the cyclic group are separated from one another by precisely one optionally substituted $CH_2$ group, and/or
wherein two atoms in the ring form a —O—O or —S—O— bond,
is excluded,
or the fragment

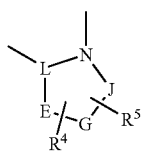

denotes the group

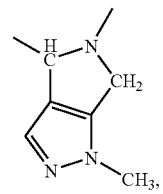

$R^{13}$ denotes a hydrogen atom or a $C_{1-5}$ alkyl group,
M denotes a phenyl, thienyl or pyridyl ring optionally substituted by $R^2$ and $R^6$, wherein
$R^2$ denotes a fluorine, chlorine, bromine or iodine atom or a methyl, ethyl, vinyl, methoxy, ethynyl, cyano or —C(O)NH$_2$ group, and
$R^6$ denotes a hydrogen, fluorine, chlorine, bromine or iodine atom or a hydroxy, methoxy, trifluoromethoxy, a $C_{1-3}$-alkyl optionally substituted by fluorine atoms, a cyano, amino or NH$_2$C(O) group,
while, unless stated otherwise, by the term "heteroaryl group" mentioned hereinbefore in the definitions is meant a monocyclic 5- or 6-membered heteroaryl group, wherein
the 6-membered heteroaryl group contains one, two or three nitrogen atoms, and
the 5-membered heteroaryl group contains an imino group optionally substituted by a $C_{1-3}$-alkyl group, or an oxygen or sulphur atom, or
an imino group optionally substituted by a $C_{1-3}$-alkyl group or an oxygen or sulphur atom and additionally one or two nitrogen atoms, or
an imino group optionally substituted by a $C_{1-3}$-alkyl group and three nitrogen atoms,
and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms,
and the bond is effected via a nitrogen atom or a carbon atom of the heterocyclic moiety or a fused-on phenyl ring,
and wherein, unless stated otherwise, by the term "halogen atom" mentioned hereinbefore in the definitions is meant an atom selected from among fluorine, chlorine, bromine and iodine,
and wherein the alkyl, alkenyl, alkynyl and alkyloxy groups contained in the previously mentioned definitions which have more than two carbon atoms may, unless stated otherwise, be straight-chain or branched and the alkyl groups in the previously mentioned dialkylated groups, for example the dialkylamino groups, may be identical or different,
and the hydrogen atoms of the methyl or ethyl groups contained in the foregoing definitions, unless stated otherwise, may be wholly or partly replaced by fluorine atoms,
the tautomers, the enantiomers, the diastereomers, the mixtures and the salts thereof.
Examples of monocyclic heteroaryl groups are the pyridyl, N-oxy-pyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, furazanyl, thienyl, thiazolyl, isothiazolyl, [1,2,3]thiadiazolyl, [1,2,4]thiadiazolyl or [1,2,5]thiadiazolyl group.

Examples of bicyclic heteroaryl groups are the benzimidazolyl, benzofuranyl, benzo[c]furanyl, benzothiophenyl, benzo[c]thiophenyl, benzothiazolyl, benzo[c]-isothiazolyl, benzo[d]isothiazolyl, benzoxazolyl, benzo[c]isoxazolyl, benzo[d]isoxazolyl, benzo[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxy-quinolinyl, isoquinolinyl, quinazolinyl, N-oxy-quinazolinyl, quinoxalinyl, phthalazinyl, indolyl, isoindolyl or 1-oxa-2,3-diaza-indenyl group.

Examples of the $C_{1-6}$-alkyl groups mentioned hereinbefore in the definitions are the methyl, ethyl, 1-propyl, 2-propyl, n-butyl, sec-butyl, tert-butyl, 1-pentyl, 2-pentyl, 3-pentyl, neo-pentyl, 3-methyl-2-butyl, 1-hexyl, 2-hexyl, 3-hexyl, 3-methyl-2-pentyl, 4-methyl-2-pentyl, 3-methyl-3-pentyl, 2-methyl-3-pentyl, 2,2-dimethyl-3-butyl or 2,3-dimethyl-2-butyl group.

Examples of the $C_{1-5}$-alkyloxy groups mentioned hereinbefore in the definitions are the methyloxy, ethyloxy, 1-propyloxy, 2-propyloxy, n-butyloxy, sec-butyloxy, tert-butyloxy, 1-pentyloxy, 2-pentyloxy, 3-pentyloxy or neo-pentyloxy group.

Examples of the $C_{2-5}$-alkenyl groups mentioned hereinbefore in the definitions are the ethenyl, 1-propen-1-yl, 2-propen-1-yl, 1-buten-1-yl, 2-buten-1-yl, 3-buten-1-yl, 1-penten-1-yl, 2-penten-1-yl, 3-penten-1-yl, 4-penten-1-yl, 1-hexen-1-yl, 2-hexen-1-yl, 3-hexen-1-yl, 4-hexen-1-yl, 5-hexen-1-yl, but-1-en-2-yl, but-2-en-2-yl, but-1-en-3-yl, 2-methyl-prop-2-en-1-yl, pent-1-en-2-yl, pent-2-en-2-yl, pent-3-en-2-yl, pent-4-en-2-yl, pent-1-en-3-yl, pent-2-en-3-yl, 2-methyl-but-1-en-1-yl, 2-methyl-but-2-en-1-yl, 2-methyl-but-3-en-1-yl or 2-ethyl-prop-2-en-1-yl group.

Examples of the $C_{2-5}$-alkynyl groups mentioned hereinbefore in the definitions are the ethynyl, 1-propynyl, 2-propynyl, 1-butyn-1-yl, 1-butyn-3-yl, 2-butyn-1-yl, 3-butyn-1-yl, 1-pentyn-1-yl, 1-pentyn-3-yl, 1-pentyn-4-yl, 2-pentyn-1-yl, 2-pentyn-3-yl, 3-pentyn-1-yl, 4-pentyn-1-yl, 2-methyl-1-butyn-4-yl, 3-methyl-1-butyn-1-yl or 3-methyl-1-butyn-3-yl group.

A second embodiment of the present invention encompasses those compounds of general formula (I), wherein E, G, J, L, M, $R^3$-$R^5$ and $R^{13}$ are defined as described in embodiment 1 and wherein
D denotes a substituted bicyclic ring system of formula

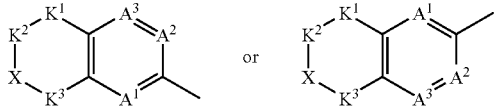

wherein
$K^1$
denotes a —$CH_2$—, —$CHR^{7a}$—, —$CR^{7b}R^{7c}$ or a —$C(O)$— group, and wherein
$R^{7a}/R^{7b}/R^{7c}$
each independently of one another denote a fluorine atom, a hydroxy, $C_{1-5}$-alkyloxy, a $C_{1-5}$-alkyl group, while the two groups $R^{7b}/R^{7c}$ may not simultaneously be bound to the cyclic carbon atom via a heteroatom, except where —$C(R^{7b}R^{7c})$— corresponds to a —$CF_2$ group, or
two groups $R^{7b}/R^{7c}$ together with the cyclic carbon atom may form a 3-membered carbocyclic group
and
$K^2$ and $K^3$ each independently of one another denote a —$CH_2$, —$CHR^{8a}$, —$CR^{8b}R^{8c}$ or a —$C(O)$— group, wherein
$R^{8a}/R^{8b}/R^{8c}$
each independently of one another denote a $C_{1-5}$-alkyl group, and/or
two groups $R^{8b}/R^{8c}$ together with the cyclic carbon atom may form a 3-membered saturated carbocyclic group
and
in all not more than four groups selected from among $R^{7a}$, $R^{7b}$, $R^{7c}$, $R^{8a}$, $R^{8b}$ and $R^{8c}$ may be present, and
X denotes an oxygen or sulphur atom, a sulphene, sulphone, —$CF_2$—, or an $NR^1$ group, wherein
$R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$ or a $C_{3-6}$-cycloalkyl group,
and wherein
$A^1$ denotes either N or $CR^{10}$,
$A^2$ denotes either N or $CR^{11}$,
$A^3$ denotes either N or CR
wherein $R^{10}$, $R^{11}$ and $R^{12}$ each independently of one another denote
a hydrogen, fluorine, chlorine, bromine or iodine atom, or a $C_{1-5}$-alkyl, $CF_3$, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group.

A third embodiment of the present invention encompasses those compounds of embodiments 1 or 2, wherein E, G, J, L, M, $R^3$-$R^5$, $R^{13}$, D, $K^1$, $K^2$ and $K^3$ are defined as in the first or second embodiment, and wherein
X denotes an $NR^1$ group, wherein
$R^1$ denotes a hydrogen atom or a $C_{1-5}$-alkyl, allyl or cyclopropyl group, and
$A^1$ denotes $CR^{10}$,
$A^2$ denotes $CR^{11}$,
$A^3$ denotes either N or $CR^{12}$,
wherein $R^{10}$, $R^{11}$ and $R^{12}$ each independently of one another denote
a hydrogen, fluorine or chlorine atom, or a methyl, $CF_3$, cyano, carboxy, $C_{1-5}$-alkyloxycarbonyl, hydroxy, methoxy, $CF_3O$, $CHF_2O$, $CH_2FO$ group.

A fourth embodiment of the present invention encompasses those compounds of general formula (I) wherein D, E, G, J, L, M, $R^3$ and $R^{13}$ are defined as described in embodiment 1, 2 or 3, and wherein
$R^4$ denotes a hydrogen atom or
a straight-chain or branched $C_{1-6}$-alkyl group,
wherein the hydrogen atoms of the methylene and/or methyl fragments of the straight-chain or branched $C_{1-6}$-alkyl group may optionally be wholly or partly replaced by fluorine atoms, and/or
wherein the hydrogen atoms of the methylene and/or methyl fragments of the straight-chain or branched $C_{1-6}$-alkyl group may optionally each be substituted independently of one another by a substituent selected from among a hydroxy, $C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino, $C_{3-6}$-cycloalkylcarbonylamino group, or
a nitrile, carboxy, aminocarbonyl, $C_{1-5}$-alkylaminocarbonyl, $C_{3-6}$-cycloalkylaminocarbonyl, di-($C_{1-5}$- alkyl)-aminocarbonyl, $C_{1-5}$-alkyloxycarbonyl or a $C_{4-7}$-cycloalkyleneiminocarbonyl group wherein a methylene group may optionally be replaced by a oxygen, sulphur or $C_{0-3}$-alkyl-substituted nitrogen atom, and if -L-E-G-J- denotes a —C—C—C—C group, $R^4$ at E or G may also denote a fluorine atom or a hydroxy, methoxy, $C_{3-5}$-alkenyloxy, $C_{3-5}$-alkynyloxy, $C_{2-5}$-alkyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-2}$-alkyloxy group, which may be substituted in the phenyl ring by 1-2 fluorine atoms or methoxy groups, an amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonylamino group, while the methyl or methylene groups present in the above-mentioned alkyl or cycloalkyl groups may each independently of one another be substituted by a substituent selected from among dimethylaminocarbonyl, $C_{1-5}$alkyloxycarbonyl, carboxy, methyl, hydroxy, methoxy or amino, with the proviso that two heteroatoms selected from among oxygen and nitrogen are separated from one another by precisely one optionally substituted $CH_2$ group, and/or that two atoms form an —O—O or —S—O— bond, is excluded, and $R^5$ denotes a hydrogen atom or a $C_{1-5}$ alkyl, allyl, propargyl or benzyl group, or if $R^5$ is linked to E or G, it may also denote a hydroxy or methoxy group or $R^4$ and $R^5$ if they are bound to the same carbon atom, may form together with the carbon atom a —C=O group, or a —$CF_2$— group, or $R^4$ and $R^5$ if they are bound to the same carbon atom or to two adjacent carbon atoms, may form together with the carbon atom(s) a 3-7-membered carbocyclic group, while one of the carbon chain members of this cyclic group may be replaced by an oxygen or sulphur atom or a —NH, —N($C_{1-5}$-alkyl), —N($C_{1-4}$-alkylcarbonyl) or a carbonyl, sulphinyl or sulphonyl group, and/or two directly adjacent carbon chain members of these $C_{4-7}$-carbocyclic groups may together be replaced by an —C(O)NH, —C(O)N($C_{1-5}$-alkyl), —S(O)$_2$NH, or —S(O)$_2$N($C_{1-5}$-alkyl) group, and/or four directly adjacent carbon chain members of these $C_{5-7}$-carbocyclic groups may together be replaced by a —O—CH$_2$—CH$_2$O group, with the proviso that a cyclic group formed from $R^4$ and $R^5$ together, wherein two nitrogen atoms or one nitrogen and one oxygen atom in the cyclic group are separated from one another by precisely one optionally substituted $CH_2$ group, and/or wherein two atoms in the ring form a —O—O or —S—O— bond, is excluded.

A fifth embodiment of the present invention encompasses those compounds of embodiments 1, 2, 3 or 4, wherein D, M, $R^3$ and $R^{13}$ are defined as described in embodiment 1, 2, 3 or 4, and wherein -L-E-G-J- denotes a —C—C—C—C group, which may be substituted by $R^4$ and $R^5$, which are defined as above in embodiments 1, 2, 3 or 4.

A sixth embodiment of the present invention encompasses those compounds of embodiments 1, 2, 3, 4 or 5, wherein D denotes a substituted bicyclic ring system of general formula

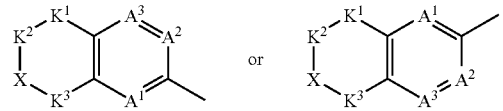

wherein $K^1$ denotes a —$CH_2$, —$CHR^{7a}$, —$CR^{7b}R^{7c}$ or a —C(O) group, wherein $R^{7a}$ denotes a $C_{1-2}$-alkyl group and $R^{7b}/R^{7c}$ each independently of one another denote a hydroxy, methoxy or a $C_{1-3}$-alkyl group, while the two groups $R^{7b}/R^{7c}$ may not simultaneously be bound to the cyclic carbon atom via an oxygen atom, or two groups $R^{7b}/R^{7c}$ together with the cyclic carbon atom may form a 3-membered carbocyclic group, and $K^2$ and $K^3$ in each case independently of one another denote a —$CH_2$, —$CHR^{8a}$ or a $CR^{8b}R^{8c}$ group, wherein $R^{8a}/R^{8b}/R^{8c}$ each independently of one another denote a $C_{1-3}$-alkyl group, and/or two groups $R^{8b}/R^{8c}$ together with the cyclic carbon atom may form a 3-membered saturated carbocyclic group and in all not more than four groups selected from among $R^{7a}$, $R^{7b}$, $R^{7c}$, $R^{8a}$, $R^{8b}$ and $R^{8c}$ may be present, and X denotes a $NR^1$ group, wherein $R^1$ denotes a hydrogen atom or a $C_{1-3}$-alkyl, allyl or cyclopropyl group, and $A^1$ denotes $CR^{10}$, $A^2$ denotes $CR^{11}$, $A^3$ denotes $CR^{12}$, wherein $R^{10}$, $R^{11}$ and $R^{12}$ each independently of one another denote a hydrogen, fluorine or chlorine atom, or a methyl, $CF_3$, hydroxy, methoxy, $CF_3O$, $CHF_2O$, $CH_2FO$ group, and -L-E-G-J- denotes a —C—C—C—C group, which may be substituted by $R^4$ and $R^5$, and $R^3$ denotes a hydrogen atom, and $R^4$ denotes a hydrogen atom or a straight-chain or branched $C_{1-3}$-alkyl group, wherein the hydrogen atoms of the methylene and/or methyl fragments of the straight-chain or branched $C_{1-6}$-alkyl group may optionally be substituted independently of one another by a substituent selected from among a hydroxy, $C_{1-5}$-alkyloxy, carboxy, $C_{1-5}$-alkyloxycarbonyl group, or if $R^4$ is bound to E or G it may also denote a fluorine atom or a hydroxy, methoxy, $C_{3-5}$-alkenyl-oxy, $C_{2-5}$-alkyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy group, with the proviso
that two heteroatoms selected from among oxygen and nitrogen are separated from one another by precisely one optionally substituted CH$_2$ group, is excluded, and R$^5$ denotes a hydrogen atom or a C$_{1-5}$ alkyl, allyl or benzyl group, or if R$^5$ is linked to E or G it may also denote a hydroxy or methoxy group, or R$^4$ and R$^5$ if they are bound to the same carbon atom, may form together with the carbon atom a —C=O group, or a —CF$_2$— group, or R$^4$ and R$^5$ if they are bound to the same carbon atom or to two adjacent carbon atoms, may form together with the carbon atom(s) a 3-6-membered carbocyclic group, while four directly adjacent carbon chain members of these C$_{5-6}$-carbocyclic groups may together be replaced by an —O—CH$_2$—CH$_2$O group, R$^{13}$ denotes a hydrogen atom, M denotes a phenyl substituted by R$^2$ in the 4-position or a pyridyl ring substituted by R$^2$ in the 5-position, wherein R$^2$ denotes a fluorine, chlorine, bromine atom, a methoxy or ethynyl group, and R$^6$ denotes a hydrogen or fluorine atom.

A seventh embodiment of the present invention encompasses those compounds of embodiments 1, 2, 3, 4, 5 or 6 wherein D, R$^3$, R$^{13}$ and M are as hereinbefore defined and wherein the central ring denotes

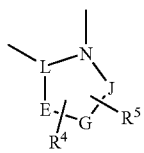

either

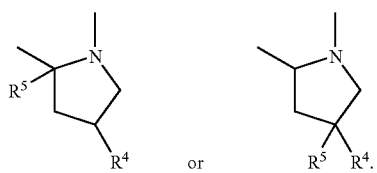

An eighth embodiment of the present invention encompasses those compounds of the embodiments 1, 2, 3, 4, 5, 6 or 7 wherein D denotes a substituted bicyclic ring system of general formula

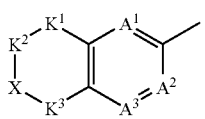

A ninth embodiment of the present invention encompasses those compounds of embodiments 1, 2, 3, 4, 5, 6, 7 or 8 which are in the R configuration at the chain members G and L of the 5-membered central ring.

According to the invention the compounds of general formula (I) are obtained by methods known per se, for example by the following methods:

(a) The Preparation of a Compound of General Formula (IIa) or (IIb)

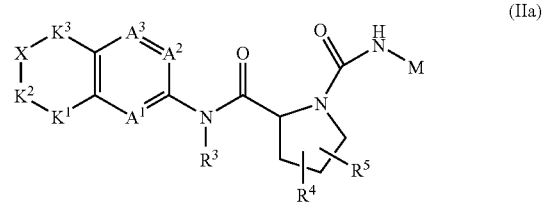
(IIa)

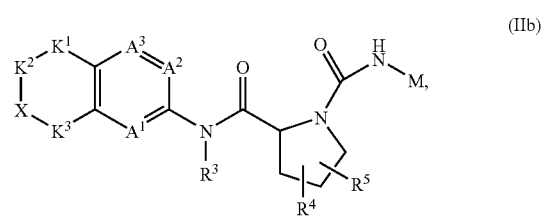
(IIb)

wherein A$^1$ to A$^3$, K$^1$ to K$^3$, M and R$^1$ to R$^6$ are defined as mentioned in embodiment 1, and which may optionally be protected at any amino, hydroxy, carboxy or thiol groups durch common protective groups such as for example those described in T. W. Greene, P. G. M. Wuts in "Protective Groups in Organic Synthesis", Wiley, 1991 and 1999, and the protective groups of which may be cleaved by methods known from the literature, is described in the examples or may be carried out for example according to one of the following formula schemes 1 and 2 or analogously to the methods of synthesis described in WO2004/87695, WO2004/87646 or in WO2003/45912.

Scheme 1

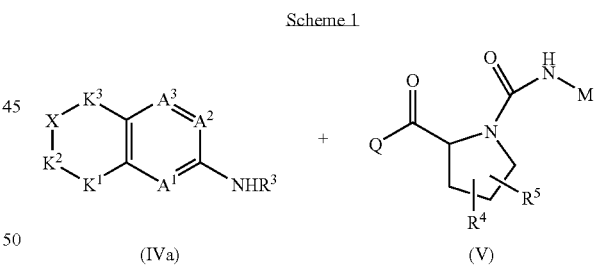

(IVa)    (V)

i) Acylation

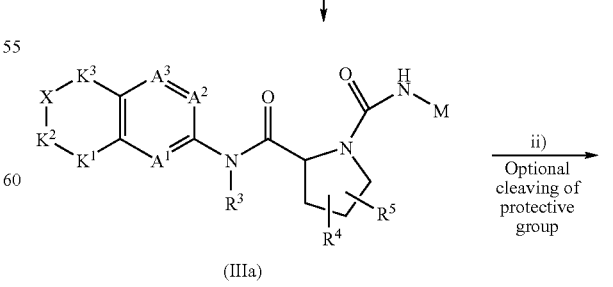

(IIIa)

ii)
Optional cleaving of protective group

Compound of Formula (IIa)

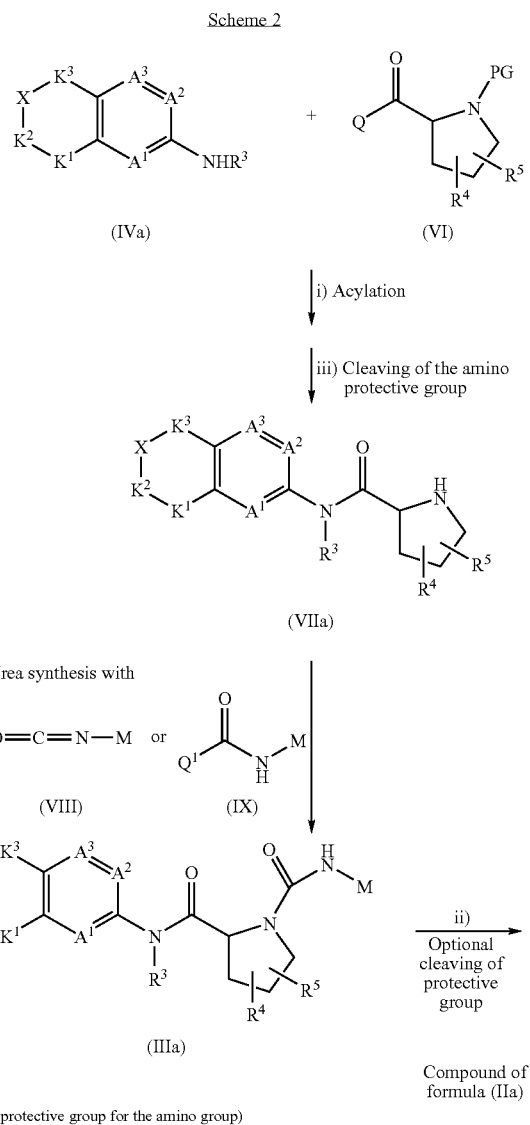

Scheme 2

(PG = protective group for the amino group)

wherein

Q/Q¹ denotes a leaving group or a group which may be converted in-situ into a leaving group, such as for example a halogen atom, a hydroxy, $C_{1-4}$-alkyloxy, alkyloxycarbonyloxy, 4-nitrophenyloxy, a trichloromethyl or acyloxy group, and PG denotes a protective group for the amino function known from the literature, such as for example a tert.-butoxycarbonyl, benzyloxycarbonyl or a trifluoroacetyl group.

The reaction steps i)-iv) shown in Schemes 1 and 2 may be carried out in the manner described in the Examples or according to the conditions known from the literature, for example as follows:

i) Acylation of an Amine (IVa) with an Optionally Activated Carboxylic Acid (V) or (VI):

The acylation is conveniently carried out with a corresponding halide or anhydride in a solvent such as methylene chloride, chloroform, carbon tetrachloride, ether, tetrahydrofuran, dioxane, benzene, toluene, acetonitrile, dimethylformamide, dimethylsulphoxide, sodium hydroxide solution or sulpholane, optionally in the presence of an inorganic or organic base at temperatures between −20 and 200° C., but preferably at temperatures between −10 and 100° C.

The acylation may however also be carried out with the free acid optionally in the presence of an acid-activating agent or a dehydrating agent, for example in the presence of ethyl-1-ethoxy-1,2-dihydroquinoline-1-carboxylate, isobutyl chloroformate, thionyl chloride, trimethylchlorosilane, hydrogen chloride, sulphuric acid, methanesulphonic acid, p-toluenesulphonic acid, phosphorus trichloride, phosphorus pentoxide, propanphosphonic acid cycloanhydride, N,N'-dicyclohexylcarbodiimide, N,N'-dicyclohexylcarbodiimide/camphorsulphonic acid, N,N'-dicyclohexylcarbodiimide/N-hydroxysuccinimide or 1-hydroxy-benzotriazole, N,N'-carbonyldiimidazole, O-(benzotriazol-1-yl)-N,N,N',N'-tetramethyl-uronium tetrafluoroborate/N-methylmorpholine, O-(benzotriazol-1-yl)-N,N,N',N'-tetramethyl-uronium tetrafluoroborate/N-ethyldiisopropylamine, O-(7-azabenzotriazol-1-yl)-N,N,N',N'-tetramethyluronium-hexafluorophosphate/N-methylmorpholine, O-pentafluorophenyl-N,N,N',N'-tetramethyluronium-hexafluorophosphate/triethylamine, N,N'-thionyldiimidazole or triphenylphosphine/carbon tetrachloride, optionally with the addition of an auxiliary base such as sodium hydroxide solution, caesium, potassium or sodium carbonate or hydrogen carbonate or an amine base such as pyridine, triethylamine, N-methylmorpholine or diisopropylethylamine at temperatures between −20 and 200° C., but preferably at temperatures between −10 and 160° C.

The acylation may also be carried out with a carboxylic acid ester (V) or (VI) and the amine (IVa) by activation with trimethylaluminium.

Other methods of amide coupling are described for example in P. D. Bailey, I. D. Collier, K. M. Morgan in "Comprehensive Functional Group Interconversions", Vol. 5, page 257 ff., Pergamon 1995, or in the Houben-Weyl Supplementary Volume 22, published by Thieme, 2003, and the literature cited therein.

ii) and iii) Cleaving a Protective Group

Any protecting group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as tetrahydrofuran, methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

However, a protective group may also be cleaved by the methods described by T. W. Greene, P. G. M. Wuts in "Protective Groups in Organic Synthesis", Wiley, 1991 and 1999.

iv) Synthesis of a Urea

The reaction of a derivative (VIIa) with an isocyanate (VII) or an optionally activated carbamic acid IX—such as for example a 4-nitrophenylcarbamic acid ester—is carried out in a solvent such as for example water, methylene chloride, chloroform, carbon tetrachloride, ether, tetrahydrofuran, dioxane, benzene, toluene, acetonitrile, dimethylformamide, dimethylsulphoxide or sulpholane or a mixture of these solvents, optionally with the addition of an auxiliary base such as sodium hydroxide solution, caesium, potassium or sodium carbonate or sodium hydrogen carbonate or an amine base such as pyridine, triethylamine, N-methylmorpholine or diisopropylethylamine at temperatures between −20 and 200° C., but preferably at temperatures between −10 and 160° C.

The compounds of general formula (IIb) may be synthesised analogously to Schemes 1 and 2 starting from component (IVb).

(b) The Components of General Formula (IVa) and (IVb)

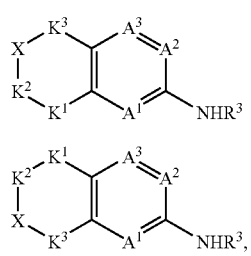

(IVa)

(IVb)

wherein $A^1$, $A^2$, $A^3$, $K^1$, $K^2$, $K^3$, X and $R^3$ are defined as in embodiment 1, and which may optionally be protected at any amino, hydroxy, carboxy or thiol groups present by common protective groups, such as for example those described in T. W. Greene, P. G. M. Wuts in "Protective Groups in Organic Synthesis", Wiley, 1991 and 1999, and the protective groups of which can be cleaved by methods known from the literature in the course of the synthesis sequence to produce compounds of formula (I), are known from the literature, or their synthesis is described in the embodiments by way of example, or they may be prepared for example using methods of synthesis known from the literature or analogously to methods of synthesis known from the literature, as described for example in WO2006/108709; S. Durand-Henchoz et al. Bull. Soc. Chim. France 1966, 11, 3413; J. P. Deer et al. Synth. Commun. 2002, 32, 2555; G. J. Quallich et al., J. Org. Chem. 1998, 63, 4116 or in J. D. Harling et al. Synth. Commun. 2001, 31, 787.

For example, compounds of general formula (IVa) and (IVb), wherein $R^3$ denotes a hydrogen atom and $A^1$, $A^2$, $A^3$, $K^1$, $K^2$, $K^3$ and X are defined as in embodiment 1, may be prepared by reduction of the nitro group of compounds of general formula (Xa) and (Xb)

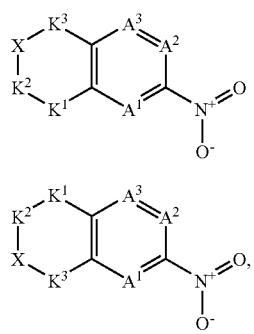

(Xa)

(Xb)

wherein $A^1$, $A^2$, $A^3$, $K^1$, $K^2$, $K^3$ and X are defined as in embodiment 1, as follows.

The reduction of the nitro group is conveniently carried out for example in a solvent or mixture of solvents such as water, aqueous ammonium chloride solution, hydrochloric acid, sulphuric acid, phosphoric acid, formic acid, acetic acid, acetanhydride with metals such as iron, zinc, tin or sulphur compounds such as ammonium sulphide, sodium sulphide or sodium dithionite or by catalytic hydrogenation with hydrogen, for example under a pressure of between 0.5 and 100 bar, but preferably between 1 and 50 bar, or with hydrazine as reducing agent, conveniently in the presence of a catalyst such as for example Raney nickel, palladium charcoal, platinum oxide, platinum on mineral fibres or rhodium, or with complex hydrides such as lithium aluminium hydride, sodium borohydride, sodium cyanoborohydride, diisobutylaluminium hydride, conveniently in a solvent or mixture of solvents such as water, methanol, ethanol, isopropanol, pentane, hexane, cyclohexane, heptane, benzene, toluene, xylene, ethyl acetate, methylpropionate, glycol, glycoldimethyl ether, diethyleneglycol dimethyl ether, dioxane, tetrahydrofuran, N-methylpyrrolidinone, or N-ethyl-diisopropylamine, N—$C_{1-5}$-alkylmorpholine, N—$C_{1-5}$-alkylpiperidine, N—$C_{1-5}$-alkylpyrrolidine, triethylamine, pyridine, for example at temperatures between −30 and 250° C., but preferably between 0 and 150° C.

(c) The components of General Formula

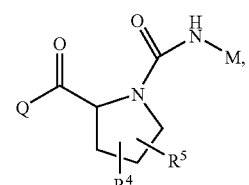

(V)

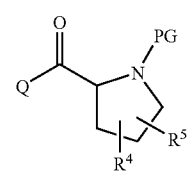

(VI)

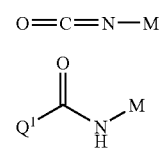

(VIII)

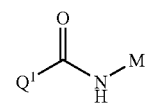

(IX)

wherein $R^4$, $R^5$, $R^6$ and $R^2$ are defined as in embodiment 1, and wherein $Q/Q^1$ denotes for example a hydroxy or $C_{1-4}$-alkyloxy group, a halogen atom, an alkyloxycarbonyloxy or acyloxy group which may optionally be protected at any amino, hydroxy, carboxy or thiol groups present by common protective groups, such as for example those described in T. W. Greene, P. G. M. Wuts in "Protective Groups in Organic Synthesis", Wiley, 1991 and 1999, and the protective groups of which can be cleaved by methods known from the literature in the course of the synthesis sequence to produce compounds of formula (I), are known from the literature, or their synthesis is described in the embodiments by way of example, or they may be prepared for example using methods of synthesis known from the literature or analogously to methods of synthesis known from the literature, as described for example in WO2004/87646, WO2003/45912, WO06/32342 or US2007/0015812.

In the reactions described above any reactive groups present such as hydroxy, carboxy, amino, alkylamino or imino groups may be protected during the reaction by conventional protecting groups which are cleaved again after the reaction.

For example, a suitable protecting group for a hydroxy group may be the methoxy, benzyloxy, trimethylsilyl, acetyl, benzoyl, tert.butyl, trityl, benzyl or tetrahydropyranyl group.

Suitable protecting groups for a carboxyl group might be the trimethylsilyl, methyl, ethyl, tert.butyl, benzyl or tetrahydropyranyl group.

Suitable protecting groups for an amino, alkylamino or imino group might be the acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, the phthalyl group.

For example, a suitable protective group for an ethynyl group may be a trimethylsilyl, diphenylmethylsilyl, tert.butyldimethylsilyl or a 1-hydroxy-1-methyl-ethyl group.

Other protective groups which may be used and their cleaving are described in T. W. Greene, P. G. M. Wuts, "Protective Groups in Organic Synthesis", Wiley, 1991 and 1999.

Any protective group used may optionally subsequently be cleaved for example by hydrolysis in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

However, a benzyl, methoxybenzyl or benzyloxycarbonyl group is cleaved hydrogenolytically, for example, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, preferably, however, 1 to 5 bar.

A methoxybenzyl group may also be cleaved in the presence of an oxidising agent such as cerium(IV)ammonium nitrate in a solvent such as methylene chloride, acetonitrile or acetonitrile/water at temperatures of between 0 and 50° C., but preferably at ambient temperature.

A methoxy group is expediently cleaved in the presence of boron tribromide in a solvent such as methylene chloride at temperatures between −35 and −25° C.

A 2,4-dimethoxybenzyl group is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

An allyloxycarbonyl group is cleaved by treating with a catalytic amount of tetrakis-(triphenylphosphine)-palladium (0), preferably in a solvent such as tetrahydrofuran and preferably in the presence of an excess of a base such as morpholine or 1,3-dimedone at temperatures between 0 and 100° C., preferably at ambient temperature and under an inert gas, or by treating with a catalytic amount of tris-(triphenylphosphine)-rhodium(I)-chloride in a solvent such as aqueous ethanol and optionally in the presence of a base such as 1,4-diazabicyclo[2.2.2]octane at temperatures between 20 and 70° C.

Moreover the compounds of general formula (I) obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g., by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides may be a (+)- or (−)-menthyloxycarbonyl, for example.

Furthermore, the compounds of formula I may be converted into the salts thereof, particularly for pharmaceutical use into the physiologically acceptable salts thereof with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

As already mentioned, the compounds of general formula I as well as the tautomers, the enantiomers, the diastereomers and the physiologically acceptable salts thereof have valuable pharmacological properties, particularly an antithrombotic activity, which is preferably based on an effect on thrombin or factor Xa, for example on a thrombin-inhibiting or factor Xa-inhibiting activity, on a prolonging effect on the aPTT time and on an inhibiting effect on related serine proteases such as e.g. urokinase, factor VIIa, factor IX, factor XI and factor XII.

The compounds listed in the experimental section may be investigated for their effect on the inhibition of factor Xa as follows:

Method:

Enzyme-kinetic measurement with chromogenic substrate. The quantity of p-nitroaniline (pNA) released from the colourless chromogenic substrate by human factor Xa is determined photometrically at 405 nm. It is proportional to the activity of the enzyme used. The inhibition of the enzyme activity by the test substance (in relation to the solvent control) is determined at various concentrations of test substance and from this the $IC_{50}$ is calculated, as the concentration which inhibits the factor Xa used by 50%.

Material:

Tris(hydroxymethyl)-aminomethane buffer (100 mMol) and sodium chloride (150 mMol), pH 8.0 plus 1 mg/ml Human Albumin Fraction V, protease-free.

Factor Xa (Calbiochem), spec. activity: 217 IU/mg, final concentration: 7 IU/ml for each reaction mixture Substrate S 2765 (Chromogenix), final concentration: 0.3 mM/l (1 KM) for each reaction mixture Test substance: final concentration 100, 30, 10, 3, 1, 0.3, 0.1, 0.03, 0.01, 0.003, 0.001 µMol/l Procedure:

10 µl of a 23.5-times concentrated starting solution of the test substance or solvent (control), 175 µl of TRIS/HSA buffer and 25 µl of a 65.8 U/L Factor Xa working solution are incubated for 10 minutes at 37° C. After the addition of 25 µl of S 2765 working solution (2.82 mMol/1) the sample is measured in a photometer (SpectraMax 250) at 405 nm for 600 seconds at 37° C.

Evaluation:

1. Determining the maximum increase (deltaOD/minutes) over 21 measuring points.
2. Determining the % inhibition based on the solvent control.
3. Plotting a dosage/activity curve (% inhibition vs substance concentration).
4. Determining the $IC_{50}$ by interpolating the X-value (substance concentration) of the dosage/activity curve at Y=50% inhibition.

All the compounds tested had an $IC_{50}$ value of less than 100 µmol/L.

The compounds prepared according to the invention are generally well tolerated.

In view of their pharmacological properties the new compounds and the physiologically acceptable salts thereof are suitable for the prevention and treatment of venous and arterial thrombotic diseases, such as for example the prevention and treatment of deep leg vein thrombosis, thrombophlebitis, for preventing reocclusions after bypass operations or angioplasty (PT(C)A), and occlusion in peripheral arterial diseases, and for preventing and treating pulmonary embolism, disseminated intravascular coagulation and severe sepsis, for preventing and treating DVT in patients with exacerbation of COPD, for treating ulcerative colitis, for treating and preventing coronary thrombosis, for preventing stroke and the occlusion of shunts.

In addition, the compounds according to the invention are suitable for antithrombotic support in thrombolytic treatment, such as for example with alteplase, reteplase, tenecteplase, staphylokinase or streptokinase, for preventing long-term restenosis after PT(C)A, for the prevention and treatment of ischaemic events in patients with all forms of coronary heart disease, for preventing metastasis and the growth of tumours and inflammatory processes, e.g. in the treatment of pulmonary fibrosis, for preventing and treating rheumatoid arthritis, for preventing and treating fibrin-dependent tissue adhesions and/or the formation of scar tissue and for promoting wound healing processes.

The compounds specified may also be used as anticoagulants in connection with the preparation, storage, fractionation or use of whole blood or in invasive therapies, e.g. for coating prostheses, artificial heart valves and catheters for reducing the risk of thrombosis.

In view of their pharmacological properties the new compounds and the physiologically acceptable salts thereof are also suitable for treating Alzheimer's and Parkinson's disease. One rationale for this can be seen for example in the following findings, from which it can be concluded that thrombin inhibitors or factor Xa inhibitors, by inhibiting thrombin formation or activity, could be valuable drugs for treating Alzheimer's and Parkinson's disease. Clinical and experimental studies indicate that neurotoxic mechanisms, for example the inflammation that accompanies the activation of proteases of the clotting cascade, are involved in the dying off of neurones following brain damage. Various studies indicate an involvement of thrombin in neurodegenerative processes, e.g. following a stroke, repeated bypass operations or traumatic brain injury. An increased thrombin activity was able to be detected for example some days after peripoheral nerve damage. It was also shown that thrombin causes neurite retraction and glia proliferation, and apoptosis in primary cultures of neurones and neuroblastoma cells (for an overview see: *Neurobiol. Aging*, 2004, 25(6), 783-793). In addition, various in vitro studies on the brains of patients with Alzheimer's disease indicate that thrombin plays a part in the pathogenesis of this disease (*Neurosci Lett.*, 1992, 146, 152-54). An accumulation of immunoreactive thrombin has been detected in neurite plaques in the brains of Alzheimer's patients. It was demonstrated in vitro that thrombin also plays a part in the regulation and stimulation of the production of Amyloid Precursor Protein (APP) as well as in the cleaving of APP into fragments which can be detected in the amyloid plaques in the brains of Alzheimer's patients. It has also been shown that thrombin-induced microglial activation in vivo leads to the degeneration of nigral dopaminergic neurones. These findings lead one to conclude that microglial activation, triggered by endogenous substance(s) such as thrombin, for example, are involved in the neuropathological process of the cell death of dopaminergic neurones, such as occurs in patients with Parkinson's disease (*J. Neurosci.*, 2003, 23, 5877-86).

The new compounds and the physiologically acceptable salts thereof can also be used for the prevention and treatment of arterial vascular diseases in combination therapy with lipid-lowering active substances such as HMG-CoA reductase inhibitors and vasodilators, particularly ACE inhibitors, angiotensin II antagonists, renin inhibitors, β-receptor antagonists, α-receptor antagonists, diuretics, Ca-channel blockers, or stimulators of soluble guanylate cyclase.

By increasing the antithrombotic activity the new compounds and the physiologically acceptable salts thereof can also be used in combination therapy with other anticoagulants such as, for example, unfractionated heparin, low-molecular heparin, fondaparinux or direct thrombin inhibitors, for example recombinant hirudine or "active-site" thrombin inhibitors.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, prasugrel, ticlopidine), with $P_2T$ receptor antagonists (e.g. cangrelor) or with combined thromboxane receptor antagonists/synthetase inhibitors (e.g. terbogrel).

The dosage required to achieve such an effect is appropriately 0.01 to 3 mg/kg, preferably 0.03 to 1.0 mg/kg by intravenous route, and 0.03 to 30 mg/kg, preferably 0.1 to 10 mg/kg by oral route, in each case administered 1 to 4 times a day.

For this purpose, the compounds of formula I prepared according to the invention may be formulated, optionally together with other active substances, with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof, to produce conventional galenic preparations such as plain or coated tablets, capsules, powders, suspensions or suppositories.

The new compounds and the physiologically acceptable salts thereof may be used therapeutically in conjunction with acetylsalicylic acid, with inhibitors of platelet aggregation such as fibrinogen receptor antagonists (e.g. abciximab, eptifibatide, tirofiban, roxifiban), with physiological activators and inhibitors of the clotting system and the recombinant analogues thereof (e.g. Protein C, TFPI, antithrombin), with inhibitors of ADP-induced aggregation (e.g. clopidogrel, ticlopidine), with $P_2T$ receptor antagonists (e.g. cangrelor) or with combined thromboxane receptor antagonists/synthetase inhibitors (e.g. terbogrel).

Experimental Section

The following Examples are intended to illustrate the invention, without restricting its scope.

As a rule, melting points and/or IR, UV, $^1$H-NMR and/or mass spectra have been obtained for the compounds prepared. Unless otherwise stated, $R_f$ values were obtained using ready-made silica gel 60 $F_{254}$ TLC plates (E. Merck, Darmstadt, Item no. 1.05714) without chamber saturation. The $R_f$ values obtained under the name Alox were determined using ready-made aluminium oxide 60 $F_{254}$ TLC plates (E. Merck, Darmstadt, Item no. 1.05713) without chamber saturation. The $R_f$ values obtained under the name Reversed-phase-8 were determined using ready-made RP-8 $F_{254s}$ TLC plates (E. Merck, Darmstadt, Item no. 1.15684) without chamber saturation. The ratios given for the eluants refer to units by volume of the solvents in question. Chromatographic purification was done using silica gel supplied by Messrs Millipore (MATREX™, 35-70 µm). If the configuration is not specified in detail, it is unclear whether the compound in question is a pure stereoisomer or a mixture of enantiomer and diastereomer.

The HPLC-MS data were obtained under the following conditions:

Method A:

Waters Alliance 2690, Waters ZQ2000 Mass Spectrometer with diode array detector 996.

The mobile phase used was:

A: water with 0.10% TFA

B: acetonitrile with 0.8% TFA

| time in min | % A | % B | flow rate in ml/min |
|---|---|---|---|
| 0.00 | 95 | 5 | 1.00 |
| 0.10 | 95 | 5 | 1.00 |
| 3.10 | 2 | 98 | 1.00 |

The stationary phase used was an X-Terra MS C18 column, 2.5 µm, 4.6 mm×30 mm.

Diode array detection took place in the wavelength range 210-500 nm.

Method B:

Waters Alliance 2695, PDA Detector 2996.

The mobile phase used was:

A: water with 0.13% TFA

B: acetonitrile

| time in min | % A | % B | flow rate in ml/min |
|---|---|---|---|
| 0.00 | 95 | 5 | 3.50 |
| 0.18 | 95 | 5 | 3.50 |
| 2.00 | 2 | 98 | 3.50 |
| 2.20 | 2 | 98 | 3.50 |

The stationary phase used was a Varian Microsorb 100 C18 column, 3 µm, 4.6 mm×30 mm.

Diode array detection took place in the wavelength range 210-380 nm.

Method C:

Waters Alliance 2695, PDA Detector 2996.

The mobile phase used was:

A: water with 0.1% HCOOH

B: acetonitrile with 0.1% HCOOH

| time in min | % A | % B | flow rate in ml/min |
|---|---|---|---|
| 0.00 | 95 | 5 | 1.60 |
| 4.50 | 10 | 90 | 1.60 |

The stationary phase used was a YMC-Pack ODS-AQ column, 3 µm, 4.6 mm×75 mm.

Method D:

Waters Alliance 2695, PDA Detector 2996.

The mobile phase used was:

A: water with 0.1% HCOOH

B: acetonitrile with 0.1% HCOOH

| time in min | % A | % B | flow rate in ml/min |
|---|---|---|---|
| 0.00 | 95 | 5 | 1.60 |
| 4.50 | 10 | 90 | 1.60 |

The stationary phase used was a Zorbax StableBond C18 column, 3 µm, 4.6 mm×75 mm.

The following abbreviations are used in the descriptions of the tests:

| | |
|---|---|
| DCM | dichloromethane |
| DIPEA | N-ethyl-diisopropylamine |
| DMF | N,N-dimethylformamide |
| EtOH | ethanol |
| sat. | saturated |
| h | hour(s) |
| HATU | O-(7-azabenzotriazol-1-yl)-N,N,N',N'-tetramethyluronium hexafluorophosphate |
| i. vac. | in vacuo |
| conc. | concentrated |
| min | minute(s) |
| NMM | N-methyl-morpholine |
| $R_f$ | retention factor |
| $R_t$ | retention time |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |

Example 1

(2R,4R)-4-methoxy-pyrrolidine-1,2-dicarboxylic acid-1-[(4-chloro-phenyl)-amide]-2-(2-methyl-1,2,3,4-tetrahydro-isoquinolin-7-yl)-amide

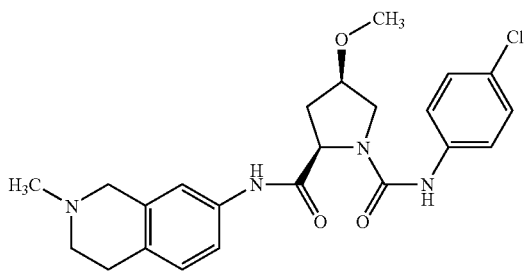

(a) (2R,4R)-4-methoxy-pyrrolidine-2-carboxylic acid (as hydrochloride)

10.3 g (48.9 mmol) 1-tert.butoxy (2R,4R)-4-methoxy-pyrrolidine-1,2-dicarboxylate are dissolved in 50 ml THF, 50 ml 6N hydrochloric acid (300 mmol) are added and the mixture is stirred for three hours. The reaction mixture is evaporated to dryness i.vac.

Yield: 7.89 g (quantitative)
$C_6H_{11}NO_3$ (145.16)×HCl
Mass spectrum: $(M+H)^+=146$ (b) (2R,4R)-1-(4-chloro-phenylcarbamoyl)-4-methoxy-pyrrolidine-2-carboxylic acid 13.5 g (87.8 mmol) 4-chloro-phenylisocyanate are added to a mixture of 7.89 g (43.9 mmol) (2R,4R)-4-methoxy-pyrrolidine-2-carboxylic acid-hydrochloride in 288 ml 5% aqueous sodium hydrogen carbonate solution and stirred for 3 h at 80° C. Another 0.6 g of the isocyanate are added and the mixture is stirred for another hour. Then the reaction mixture is cooled and filtered to remove the solid. The solid is washed with water. The aqueous phases are combined and acidified with 6N aqueous hydrochloric acid. Then the mixture is extracted three times with dichloromethane. The combined organic phases are dried on sodium sulphate, filtered and evaporated to dryness i. vac.

Yield: 10.0 g (76%)
$R_f$ value: 0.47 ($R^P$-8; methanol/5% sodium chloride solution 6:4)
$C_{13}H_{15}ClN_2O_4$ (298.72)
Mass spectrum: $(M+H)^+=299/301$ (chlorine isotopes)

(c) (2R,4R)-4-methoxy-pyrrolidine-1,2-dicarboxylic acid-1-[(4-chloro-phenyl)-amide]-2-(2-methyl-1,2,3,4-tetrahydro-isoquinolin-7-yl)-amide 248 mg (0.266 mmol) 2-ethoxy-1-ethoxycarbonyl-1,2-dihydroquinoline are added to a solution of 299 mg (1 mmol) (2R,4R)-1-(4-chloro-phenylcarbamoyl)-4-methoxy-pyrrolidine-2-carboxylic acid in 2 ml THF and stirred for 30 min. Then 162 mg (1 mmol) 2-methyl-1,2,3,4-tetrahydroisoquinolin-7-ylamine are added and the mixture is stirred for 18 hours at reflux temperature.

The reaction mixture is concentrated i. vac. and purified by chromatography on silica gel (eluant: DCM/(ethanol/ammonia 95:5) 96:4-94:6).

Yield: 15 mg (3%)
$R_f$ value: 0.41 (silica gel; dichloromethane/ethanol/ammonia=90:10:1)
$C_{23}H_{27}ClN_4O_3$ (442.94)
Mass spectrum: $(M+H)^+=443/445$ (chlorine isotopes)
The following compounds may be prepared analogously:

| Ex. | Structural formula | Yield | Mass peak(s) | DC/HPLC |
|---|---|---|---|---|
| 2 | | 25% | $(M-H)^-=$ 441/443 (chlorine isotopes) | $R_f$ value: 0.37 (silica gel; DCM/EtOH/NH$_3$ = 90:10:1) |

(2R,4R)-4-methoxy-pyrrolidine-1,2-dicarboxylic acid-1-[(4-chloro-phenyl)-amide]-2-(2-methyl-1,2,3,4-tetrahydro-isoquinolin-6-yl)-amide

| Ex. | Structural formula | Yield | Mass peak(s) | DC/HPLC |
|---|---|---|---|---|
| 3 | (2R,4R)-4-methoxy-pyrrolidine-1,2-dicarboxylic acid-1-[(4-chloro-phenyl)-amide]-2-(1,2-dimethyl-1,2,3,4-tetrahydro-isoquinolin-6-yl)-amide | 57% | $(M + H)^+$ = 457/459 (chlorine isotopes) | $R_t$ = 2.80 min (Method A) |
| 8 | (R)-pyrrolidine-1,2-dicarboxylic acid-1-[(4-chloro-phenyl)-amide]-2-(1-oxo-1,2,3,4-tetrahydro-isoquinolin-7-yl)-amide | 41% | $(M + H)^+$ = 413/415 (chlorine isotopes) | $R_t$ = 1.18 min (Method B) |

Example 4

(2S,4R)-4-methoxy-2-methyl-pyrrolidine-1,2-dicarboxylic acid-1-[(4-chloro-phenyl)-amide]-2-[(2-methyl-1,2,3,4-tetrahydro-isoquinolin-6-yl)-amide (as the trifluoroacetate salt)

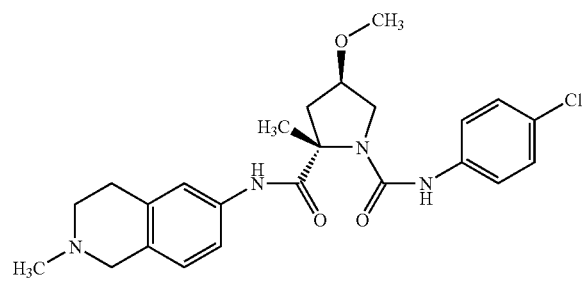

(a) 1-tert.-butyl-2-methyl (2S/R,4R)-4-methoxy-2-methyl-pyrrolidine-1,2-dicarboxylate 21.4 ml (1.6 M in n-hexane, 34.2 mmol) n-butyllithium solution are added dropwise at ~5° C. to a solution of 4.8 ml (34.2 mmol) diisopropylamine in 200 ml THF and stirred for 10 min. Then the mixture is cooled to −35° C. and combined with a solution of 5.8 g (22.4 mmol) 1-tert.-butyl-2-methyl (2S,4R)-4-methoxy-2-methyl-pyrrolidine-1,2-dicarboxylate in 200 ml THF. The mixture is heated to 0° C. within one hour and then cooled to −78° C. 2.1 ml (33.7 mmol) methyliodide are added dropwise and the mixture is stirred for 4 hours at −78° C. Then 3 ml sat. ammonium chloride solution are added dropwise and the mixture is heated to RT. Then it is mixed with water and extracted three times with ethyl acetate. The combined organic phases are dried on sodium sulphate, filtered and evaporated down i. vac. The residue is purified by column chromatography on silica gel (DCM/MeOH 4:1).

Yield: 4.2 g (69%)
$R_f$ value: 0.38 (silica gel; dichloromethane/methanol=80:20)
$C_{13}H_{23}NO_5$ (273.33)
Mass spectrum: $(M+H)^+$=274

(b) methyl (2S/R,4R)-4-methoxy-2-methyl-pyrrolidine-2-carboxylate (trifluoroacetate salts)

800 mg (293 µmol) 1-tert.-butyl-2-methyl (2S/R,4R)-4-methoxy-2-methyl-pyrrolidine-1,2-dicarboxylate are dissolved in 2.5 ml DCM, combined with 2.5 ml TFA and stirred for 16 hours at RT. The reaction mixture is evaporated to dryness i. vac.

Yield: quantitative
$R_t$ value: 0.42 min (Method B)
$C_8H_{15}NO_3$ (173.21)
Mass spectrum: $(M+H)^+$=174

(c) 1-benzyl-2-methyl (2S,4R)-4-methoxy-2-methyl-pyrrolidine-1,2-dicarboxylate 419 mg (146 µmol) methyl (2S/R,4R)-4-methoxy-2-methyl-pyrrolidine-2-carboxylate (as the trifluoroacetate salts) are dissolved in 4.5 ml DCM, combined at 0° C. with 0.5 ml (292 µmol) DIPEA and then combined with 0.3 ml (175 µmol) benzyl chloroformate. The mixture is stirred for 10 min at 0° C. and then for 16 hours at RT. Then the reaction mixture is evaporated down i. vac. and purified by RP-HPLC.

Yield: 114 mg (50%)
$R_t$ value: 1.37 min (Method B)
$C_{16}H_{21}NO_5$ (307.34)
Mass spectrum: $(M+H)^+$=308

The following is additionally obtained:

1-benzyl-2-methyl (2R,4R)-4-methoxy-2-methyl-pyrrolidine-1,2-dicarboxylate

Yield: 114 mg (50%)
$R_t$ value: 1.41 min (Method B)
$C_{16}H_{21}NO_5$ (307.34)
Mass spectrum: $(M+H)^+=308$ (d) 1-benzyl (2S,4R)-4-methoxy-2-methyl-pyrrolidine-1,2-dicarboxylate 114 mg (370 μmol) 1-benzyl-2-methyl (2S,4R)-4-methoxy-2-methyl-pyrrolidine-1,2-dicarboxylate are dissolved in 1 ml of methanol and combined with 2.4 ml (605 μmol) 8% aqueous lithium hydroxide solution. The reaction mixture is stirred for three days at RT and then evaporated down i.vac. The residue is acidified with 1N HCl and extracted three times with ethyl acetate. The combined organic phases are dried on sodium sulphate, filtered and evaporated down i. vac.

Yield: 100 mg (92%)
$R_t$ value: 1.25 min (Method B)
$C_{15}H_{19}NO_5$ (437.54)
Mass spectrum: $(M+H)^+=294$ (e) benzyl (2S,4R)-4-methoxy-2-methyl-2-(2-methyl-1,2,3,4-tetrahydro-isoquinolin-6-ylcarbamoyl)-pyrrolidine-1-carboxylate (as the trifluoroacetate salt)

56 mg (345 μmol) 1-benzyl (2S,4R)-4-methoxy-2-methyl-pyrrolidine-1,2-dicarboxylate are dissolved in 0.5 ml DMF and combined with 134 mg (352 μmol) HATU and with 160 μl NMM. The mixture is stirred for 15 min at RT and then combined with 100 mg (341 μmol) 2-methyl-1,2,3,4-tetrahydroisoquinolin-6-ylamine. The reaction mixture is stirred for three hours at RT and then acidified with TFA. The product is isolated from this mixture by RP-HPLC.

Yield: 104 mg (54%)
$R_t$ value: 1.16 min (Method B)
$C_{25}H_{31}N_3O_4$ (437.54)×$CF_3CO_2H$
Mass spectrum: $(M+H)^+=438$ (f) (2S,4R)-4-methoxy-2-methyl-pyrrolidine-2-carboxylic acid-(2-methyl-1,2,3,4-tetrahydro-isoquinolin-6-yl)-amide (as the trifluoroacetate salt)

104 mg (345 μmol) benzyl (2S,4R)-4-methoxy-2-methyl-2-(2-methyl-1,2,3,4-tetrahydro-isoquinolin-6-ylcarbamoyl)-pyrrolidine-1-carboxylate (as the trifluoroacetate salt) are dissolved in a mixture of 6 ml THF and 6 ml of methanol, combined with 30 mg palladium/charcoal (10%) and hydrogenated for 2.5 hours with 3 bar hydrogen. Then the mixture is filtered and evaporated down i. vac.

Yield: 75 mg (96%)
$R_t$ value: 0.32 min (Method B)
$C_{17}H_{25}N_3O_2$ (303.41)×$CF_3CO_2H$
Mass spectrum: $(M+H)^+=304$ (g) (2S,4R)-4-methoxy-2-methyl-pyrrolidine-1,2-dicarboxylic acid-1-[(4-chloro-phenyl)-amide]-2-[(2-methyl-1,2,3,4-tetrahydro-isoquinolin-6-yl)-amide
(as the trifluoroacetate salt)

75 mg (180 μmol) (2S,4R)-4-methoxy-2-methyl-pyrrolidine-2-carboxylic acid-(2-methyl-1,2,3,4-tetrahydro-isoquinolin-6-yl)-amide (as the trifluoroacetate salt) are dissolved in 1.5 ml DMF and combined with 122 μl (796 μmol) NMM. Then 30 mg (195 μmol) 4-chloro-phenylisocyanate are added, and the mixture is stirred for three days at RT. Then it is acidified with TFA. The product is isolated from this mixture by RP-HPLC.

Yield: 62 mg (60%)
$R_t$ value: 1.17 min (Method B)
$C_{24}H_{29}ClN_4O_3$ (456.98)×$CF_3CO_2H$
Mass spectrum: $(M+H)^+=457/459$ (chlorine isotopes)
The following compound may be prepared analogously:

| Ex. | Structural formula | Yield | Mass peak(s) | DC/HPLC |
| --- | --- | --- | --- | --- |
| 5 | 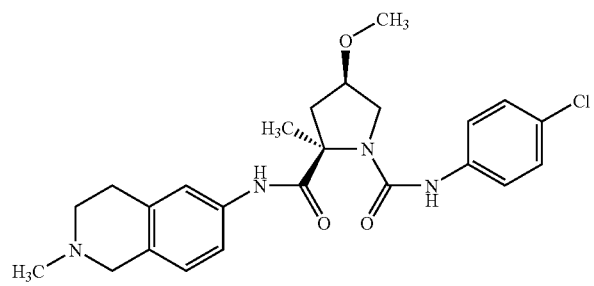 | 11.4% | $(M+H)^+ =$ 457/459 (chlorine isotopes) | $R_t = 1.15$ min (Method B) |

(2R,4R)-4-methoxy-2-methyl-pyrrolidine-1,2-dicarboxylic acid-1-[(4-chloro-phenyl)-amide]-2-[(2-methyl-1,2,3,4-tetrahydro-isoquinolin-6-yl)-amide (as the trifluoroacetate salt)

Example 6

(2R,4R)-4-methoxy-pyrrolidine-1,2-dicarboxylic acid-1-[(5-chloro-pyridin-2-yl)-amide]-2-(2-methyl-1,2,3,4-tetrahydro-isoquinolin-6-yl)-amide (as the trifluoroacetate salt)

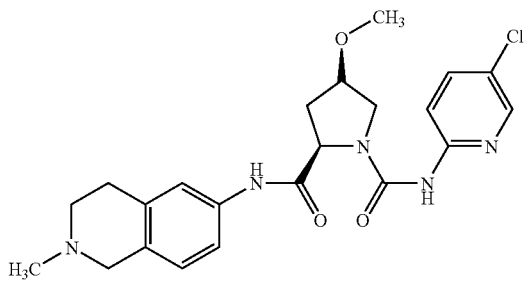

(a) benzyl (2R,4R)-4-methoxy-2-(2-methyl-1,2,3,4-tetrahydro-isoquinolin-6-ylcarbamoyl)-pyrrolidine-1-carboxylate (as the trifluoroacetate salt)

100 mg (616 µmol) 2-methyl-1,2,3,4-tetrahydro-isoquinolin-6-ylamine are dissolved in 1.5 ml DCM and at RT combined with 0.61 ml (1.22 mmol) trimethylaluminium solution (2M in toluene) and stirred for 15 min. This reaction mixture is added to 180 mg (614 µmol) 1-benzyl-2-methyl (2R,4R)-4-methoxy-pyrrolidine-1,2-dicarboxylate and rinsed with 0.5 ml DCM. The reaction mixture is stirred for three hours at RT and then added to 2N sodium hydroxide solution. The aqueous phase is extracted three times with ethyl acetate. The combined organic phases are dried on sodium sulphate, filtered and evaporated to dryness i.vac. The residue is purified by RP-HPLC.

Yield: 169 mg (51%)
$R_t$ value: 1.05 min (Method B)
$C_{24}H_{29}N_3O_4$ (423.52)×$CF_3CO_2H$
Mass spectrum: $(M+H)^+=424$

(b) (2R,4R)-4-methoxy-pyrrolidine-2-carboxylic acid-(2-methyl-1,2,3,4-tetrahydro-isoquinolin-6-yl)-amide (as the trifluoroacetate salt)

168 mg (313 µmol) benzyl (2R,4R)-4-methoxy-2-(2-methyl-1,2,3,4-tetrahydro-isoquinolin-6-ylcarbamoyl)-pyrrolidine-1-carboxylate (as the trifluoroacetate salt) are hydrogenated analogously to Example 4f.

Yield: 120 mg (95%)
$R_t$ value: 0.31 min (Method B)
$C_{16}H_{23}N_3O_2$ (289.38)×$CF_3CO_2H$
Mass spectrum: $(M+H)^+=290$

(c) (2R,4R)-4-methoxy-pyrrolidine-1,2-dicarboxylic acid-1-[(5-chloro-pyridin-2-yl)-amide]-2-(2-methyl-1,2,3,4-tetrahydro-isoquinolin-6-yl)-amide (as the trifluoroacetate salt)

170 mg (843 µmol) 4-nitrophenyl chloroformate are added to a solution of 100 mg (778 µmol) 2-amino-5-chloro-pyridine in 2 ml DCM and 70 µl (867 µmol) pyridine and the mixture is stirred for 3.5 hours. Then the reaction mixture is evaporated to dryness and added as crude product to a solution of 120 mg (297 µmol) (2R,4R)-4-methoxy-pyrrolidine-2-carboxylic acid-(2-methyl-1,2,3,4-tetrahydro-isoquinolin-6-yl)-amide (as the trifluoroacetate salt) and 125 µl (900 µmol) TEA in 2.5 ml DMF. The reaction mixture is stirred for three days at RT and then combined with sat. sodium hydrogen carbonate solution. The aqueous phase is extracted three times with ethyl acetate.

The combined organic phases are dried on sodium sulphate, filtered and evaporated to dryness i.vac. The residue is purified by RP-HPLC.

Yield: 54 mg (32%)
$R_t$ value: 0.94 min (Method B)
$C_{22}H_{26}ClN_5O_3$ (443.94)×$CF_3CO_2H$
Mass spectrum: $(M+H)^+=444/446$ (chlorine isotopes)

The following compounds may be prepared analogously:

| Ex. | Structural formula | Yield | Mass peak(s) | DC/HPLC |
|---|---|---|---|---|
| 9 | 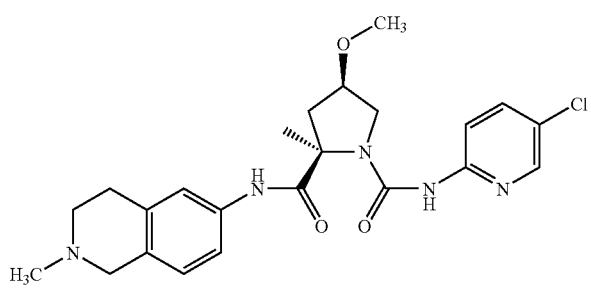<br>(2R,4R)-4-methoxy-pyrrolidin-2-methyl-1,2-dicarboxylic acid-1-[(5-chloro-pyridin-2-yl)-amide]-2-(2-methyl-1,2,3,4-tetrahydro-isoquinolin-6-yl)-amide | 35% | $(M+H)^+=$ 458/460 (chlorine isotopes) | $R_t$ value: 1.04 min Method B |

| Ex. | Structural formula | Yield | Mass peak(s) | DC/HPLC |
|---|---|---|---|---|
| 10 | (2R)-pyrrolidine-1,2-dicarboxylic acid-1-[(5-chloro-pyridin-2-yl)-amide]-2-(2-methyl-1,2,3,4-tetrahydro-isoquinolin-6-yl)-amide | 15% | (M + H)⁺ = 428/430 (chlorine isotopes) | $R_f$ value: 0.98 min Method B |

Example 11

(2R,4R)-4-methoxy-pyrrolidine-1,2-dicarboxylic acid-1-[(4-bromo-phenyl)-amide]-2-[(2,3-dimethyl-1,2,3,4-tetrahydro-isoquinolin-6-yl)-amide (mixture of diastereomers)

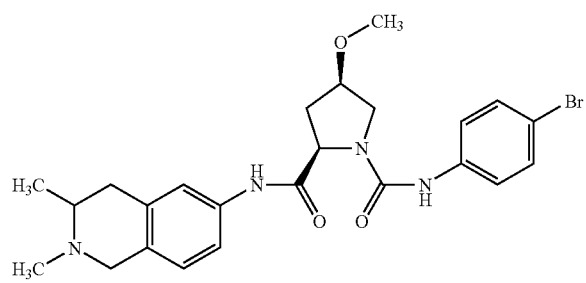

(a) acetic acid-(3-methyl-1,2,3,4-tetrahydro-isoquinolin-6-yl)-amide

A mixture of 2.2 ml (31 mmol) dioxolane, 1.2 g (9.6 mmol) piperidine hydrochloride, 1.78 g (7.8 mmol) acetic acid-[3-(2-aminopropyl)phenyl]amide and 5 μl conc. HCl are heated to 90° C. for 7.5 h. After cooling, water and ethyl acetate are added, the aqueous phase is made basic with 2 N NaOH and extracted 3× with ethyl acetate. After drying the organic phases with $Na_2SO_4$ the mixture is concentrated and purified by column chromatography (silica gel; $CH_2Cl_2$/EtOH:$NH_4OH$ 95:5 110/0->4/1).

$R_f$ value: 0.15 (silica gel; dichloromethane/ethanol/$NH_4OH$=80:20:2)
$C_{12}H_{16}N_2O$ (204.27)
Mass spectrum: (M+H)⁺=205.

(b) acetic acid-(2,3-dimethyl-1,2,3,4-tetrahydro-isoquinolin-6-yl)-amide formate 0.71 g (3.5 mmol) acetic acid-(3-methyl-1,2,3,4-tetrahydro-isoquinolin-6-yl)-amide in 2.0 ml formic acid are combined with 0.31 ml 37% formalin solution in water, with stirring, at ambient temperature, and stirred for 4.5 h at 70° C. The reaction mixture is concentrated, ethanol is added several times and the mixture is concentrated again.

$R_f$ value: 0.23 (silica gel; dichloromethane/ethanol/$NH_4OH$=80:20:2)
$C_{12}H_{16}N_2O\times CH_2O_2$ (264.32)
Mass spectrum: (M+H)⁺=219.

(c) 6-amino-2,3-dimethyl-1,2,3,4-tetrahydro-isoquinoline dihydrochloride 0.98 g (3.7 mmol) acetic acid-(2,3-dimethyl-1,2,3,4-tetrahydro-isoquinolin-6-yl)-amide are combined with a total of 15 ml 6N HCl over a period of several hours and stirred for a total of 16 h. Then the reaction mixture is concentrated in vacuo.

$R_f$ value: 0.84 ($R^P$-8; methanol/5% NaCl solution=6:4)
$C_{11}H_{16}N_2\times 2HCl$ (249.18)
Mass spectrum: (M+H)⁺=177.

(d) (2R,4R)-4-methoxy-pyrrolidine-1,2-dicarboxylic acid-1-[(4-bromo-phenyl)-amide]-2-[(2,3-dimethyl-1,2,3,4-tetrahydro-isoquinolin-6-yl)-amide (mixture of diastereomers)

The title compounds are prepared from 6-amino-2,3-dimethyl-1,2,3,4-tetrahydro-isoquinoline dihydrochloride and 1-benzyl (2R,4R)-4-methoxy-2-methyl-pyrrolidine-1,2-dicarboxylate and 4-bromophenylisocyanate according to reaction sequence 4e, 4f, 4g.

$R_f$ value: 0.42 (RP-8; methanol/5% NaCl solution=6:4)
$C_{24}H_{29}BrN_4O_3$ (501.42)
Mass spectrum: (M+H)⁺=501/503 (bromine isotopes).

Examples 12 and 13

(2R,4R)-4-methoxy-pyrrolidine-1,2-dicarboxylic acid-1-[(4-bromo-phenyl)-amide]-2-[(3S)-(2,3-dimethyl-1,2,3,4-tetrahydro-isoquinolin-6-yl)-amide and (2R,4R)-4-methoxy-pyrrolidine-1,2-dicarboxylic acid-1-[(4-bromo-phenyl)-amide]-2-[(3R)-(2,3-dimethyl-1,2,3,4-tetrahydro-isoquinolin-6-yl)-amide

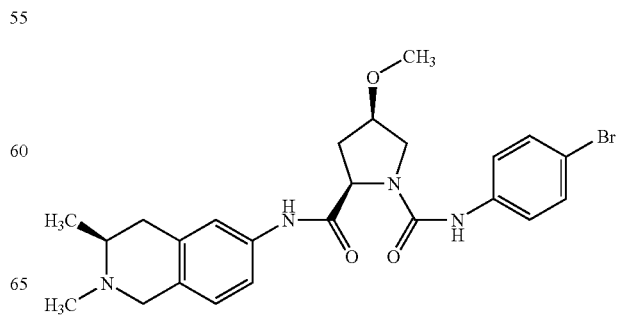

-continued

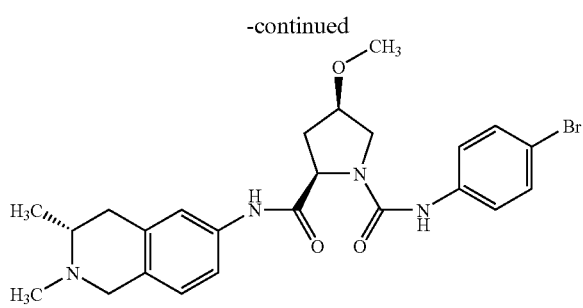

The two pure stereoisomers may be prepared analogously to Example 11. For this purpose, acetic acid-(3-methyl-1,2,3,4-tetrahydro-isoquinolin-6-yl)-amide is separated into its enantiomers by preparative column chromatography with a chiral stationary phase (Supercritical Fluid Chromatography: DAICEL-ADH column, 250 mm×20 mm; flow 70 ml/min; eluant: supercritical $CO_2$/methanol+0.2% dimethylamine 87/13, Enantiomer 1 $R_t$ value: 5.8 min; Enantiomer 2 $R_t$ value: 6.7 min) and then the individual enantiomers are reacted according to the reaction sequence described in Example 11 to yield the title compounds.

Diastereomer 1

$R_f$ value: 0.39 (RP-8; methanol/5% NaCl solution=6:4)
$C_{24}H_{29}BrN_4O_3$ (501.42)
Mass spectrum: $(M+H)^+=501/503$ (bromine isotopes).

Diastereomer 2

$R_f$ value: 0.39 (RP-8; methanol/5% NaCl solution=6:4)
$C_{24}H_{29}BrN_4O_3$ (501.42)
Mass spectrum: $(M+H)^+=501/503$ (bromine isotopes).

Example 14

(2R,4R)-4-methoxy-pyrrolidine-1,2-dicarboxylic acid-1-[(4-chloro-phenyl)-amide]-2-[(1,2-dimethyl-1,2,3,4-tetrahydro-isoquinolin-6-yl)-amide (mixture of diastereomers)

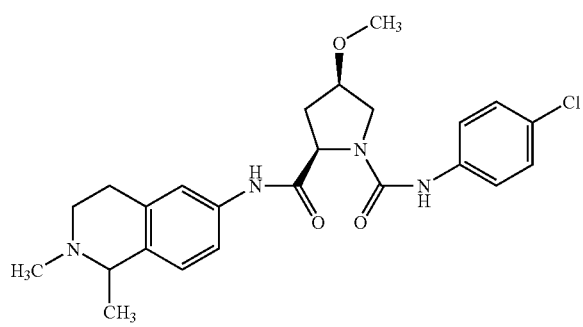

(a) methyl (1-methyl-3,4-dihydro-isoquinoline-6-yl)-carbamate

A mixture of 4.13 g (17.5 mmol) methyl N-[3-(2-methyl-carbonylamino-ethyl)phenyl]carbamate and 35 ml chloroform is slowly combined with 8.00 g (38.4 mmol) phosphorus pentachloride and the mixture is stirred for 16 h. Then the mixture is carefully poured into water and stirred for 45 min. It is extracted 3× with methylene chloride and then the aqueous phase is made basic with 4N NaOH. The crystals precipitated are suction filtered and dried.

Yield: 2.6 g (68%)
Mass spectrum: $(M+H)^+=219$ (b) methyl (1,2-dimethyl-1,2,3,4-tetrahydro-isoquinoline-6-yl)-carbamate A mixture of 1.00 g (4.5 mmol) methyl (1-methyl-3,4-dihydro-isoquinolin-6-yl)-carbamate, 2.3 ml (37 mmol) methyl iodide and 25 ml EtOAc is stirred for 72 h. The crystals precipitated are filtered off, taken up in 10 ml of methanol and 140 mg (3.6 mmol) sodium borohydride are added batchwise. After 2 h the mixture is concentrated and purified by chromatography (silica gel; dichloromethane/methanol 90:10).

Yield: 93%
Mass spectrum: $(M+H)^+=236$
$R_t$ value: 0.78 min Method B (c) 6-amino-1,2-dimethyl-1,2,3,4-tetrahydro-isoquinoline hydrobromide A mixture of 110 mg (0.47 mmol) methyl (1,2-dimethyl-1,2,3,4-tetrahydro-isoquinolin-6-yl)-carbamate, 2.0 Ml 33% HBr in glacial acetic acid and 2.0 ml glacial acetic acid are heated to boiling for 1.5 h. Then the mixture is concentrated in vacuo, mixed with water and the aqueous phase is separated off and freeze-dried.

Mass spectrum: $(M+H)^+=177$
$R_t$ value: 0.28 min Method B (d) (2R,4R)-4-methoxy-pyrrolidine-1,2-dicarboxylic acid-1-[(4-chloro-phenyl)-amide]-2-[(1,2-dimethyl-1,2,3,4-tetrahydro-isoquinolin-6-yl)-amide× $CF_3COOH$ (mixture of diastereomers)

A mixture of 100 mg 6-amino-1,2-dimethyl-1,2,3,4-tetrahydro-isoquinoline hydrobromide, 90 mg (0.30 mmol) (2R,4R)-1-(4-chloro-phenylcarbamoyl)-4-methoxy-pyrrolidine-2-carboxylic acid and 0.25 ml triethylamine in 5 ml THF is slowly combined with 0.71 ml 50% propanephosphonic acid cycloanhydride in ethyl acetate and heated to 75° C. for 3 h. Then the reaction mixture is concentrated in vacuo, acidified with TFA and purified by chromatography.

$R_t$ value: 1.13 min (Method B)
$C_{24}H_{29}ClN_4O_3$ (456.97)×$CF_3CO_2H$
Mass spectrum: $(M+H)^+=457/459$ (chlorine isotopes)

Example 15 and 16

(2R,4R)-4-methoxy-pyrrolidine-1,2-dicarboxylic acid-1-[(4-bromo-phenyl)-amide]-2-[(R)-(1,2-dimethyl-1,2,3,4-tetrahydro-isoquinolin-6-yl)-amide and (2R,4R)-4-methoxy-pyrrolidine-1,2-dicarboxylic acid-1-[(4-bromo-phenyl)-amide]-2-[(S)-(1,2-dimethyl-1,2,3,4-tetrahydro-isoquinolin-6-yl)-amide

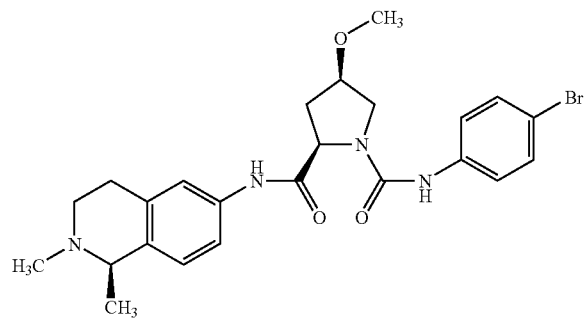

The two pure stereoisomers may be prepared analogously to Example 14. To do this, 6-amino-1,2-dimethyl-1,2,3,4-tetrahydro-isoquinoline hydrobromide is separated into the enantiomers by preparative column chromatography with a chiral stationary phase (DAICEL OJ-H, 250 mm×20 mm, 5 μM, hexane+0.2% cyclohexylamine/isopropanol 60/40, flow rate 15 ml/min, enantiomer 1 $R_t$ value: 9.2 min; enantiomer 2 $R_t$ value: 14.1 min) and then the individual enantiomers are reacted according to the reaction sequence described in Example 14 to obtain the title compounds.

Diastereomer 1

$R_t$ value: 1.20 min (Method B)

$C_{24}H_{29}BrN_4O_3$ (501.42)×$CF_3CO_2H$

Mass spectrum: $(M+H)^+$=501/503 (bromine isotopes)

Diastereomer 2

$R_t$ value: 1.19 min (Method B)

$C_{24}H_{29}BrN_4O_3$ (501.42)×$CF_3CO_2H$

Mass spectrum: $(M+H)^+$=501/503 (bromine isotopes)

Example 52

(2R,4R)-4-methoxy-pyrrolidine-1,2-dicarboxylic acid-1-[(4-chloro-phenyl)-amide]-2-[(2-methyl-1,2,3,4-tetrahydro-8-aza-isoquinolin-6-yl)-amide (a) 2-methyl-6-nitro-1,2,3,4-tetrahydro-8-aza-isoquinoline A mixture of 400 mg (2.0 mmol) 1-methyl-3,5-dinitropyridone, 300 mg 1-methyl-piperidin-3-one and 15 ml 2M ammonia in methanol are heated to 60° C. for 20 h. It is concentrated and purified by chromatography (silica gel, $CH_2Cl_2$/MeOH 98/2).

Yield: 15%

$R_t$ value: 0.25 min (Method B)

Mass spectrum: $(M+H)^+$=194

(b) 2-methyl-6-amino-1,2,3,4-tetrahydro-8-aza-isoquinoline

A mixture of 75 mg (0.311 mmol) 2-methyl-6-nitro-1,2,3,4-tetrahydro-8-aza-isoquinoline, 50 mg Raney nickel and 10 ml of methanol is reduced for 4 h at 3 bar hydrogen pressure. Then it is filtered and evaporated down.

Yield: quantitative $R_f$ value: 0.1 (silica gel; $CH_2Cl_2$/methanol 9/1)

Mass spectrum: $(M+H)^+$=164

(c) (2R,4R)-4-methoxy-pyrrolidine-1,2-dicarboxylic acid-1-[(4-chloro-phenyl)-amide]-2-[(2-methyl-1,2,3,4-tetrahydro-8-aza-isoquinolin-6-yl)-amide× $CF_3COOH$ The title compound is obtained from 2-methyl-6-amino-1,2,3,4-tetrahydro-8-aza-isoquinoline analogously to Example 14d.

$R_t$ value: 1.03 min (Method B)

$C_{22}H_{26}ClN_5O_3$ (443.93)×$CF_3CO_2H$

Mass spectrum: $(M+H)^+$=444/446 (chlorine isotopes)

Example 53

(2R,4R)-4-methoxy-2-methyl-pyrrolidine-1,2-dicarboxylic acid-1-[(5-chloro-pyridin-2-yl)-amide]-2-[(2-methyl-1,2,3,4-tetrahydro-8-aza-isoquinolin-6-yl)-amide

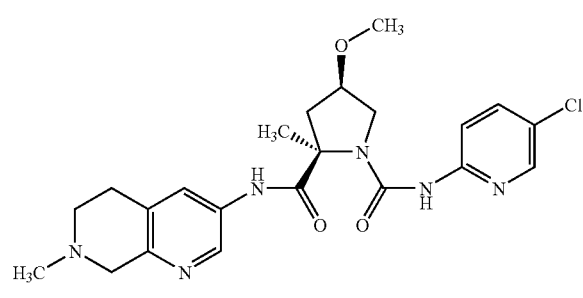

The title compound is obtained from 2-methyl-6-amino-1,2,3,4-tetrahydro-8-aza-isoquinoline analogously to Example 6a, 6b, 6c.

$R_f$ value: 0.96 min (Method B)
$C_{22}H_{27}ClN_6O_3$ (458.94)×$CF_3CO_2H$
Mass spectrum: $(M+H)^+$=459/461 (chlorine isotopes)

Example 54

(2R,4R)-4-methoxy-pyrrolidine-1,2-dicarboxylic acid-1-[(4-chloro-phenyl)-amide]-2-[(2-methyl-1,2,3,4-tetrahydro-5-aza-isoquinolin-7-yl)-amide× $CF_3COOH$

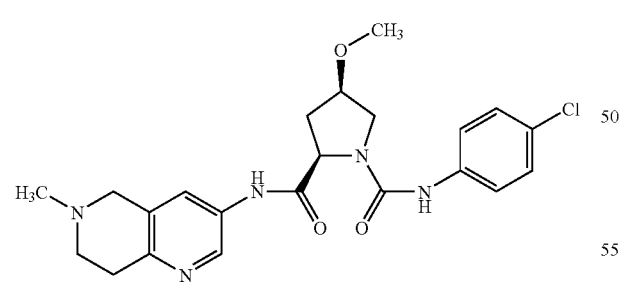

2-methyl-7-amino-1,2,3,4-tetrahydro-5-aza-isoquinoline was prepared analogously to Example 52 a and 52b from 1-methyl-3,5-dinitro-pyridone and 1-methyl-piperidin-4-one and reacted according to Example 14d to form the title compound.

$R_f$ value: 0.99 min (Method B)
$C_{22}H_{26}ClN_5O_3$ (458.94)×$CF_3CO_2H$
Mass spectrum: $(M+H)^+$=444/446 (chlorine isotopes)

Example 55

(2R,4R)-4-methoxy-pyrrolidine-1,2-dicarboxylic acid-1-[(4-chloro-phenyl)-amide]-2-[(1,2-dimethyl-1,2,3,4-tetrahydro-8-aza-isoquinolin-6-yl)-amide× $CF_3COOH$

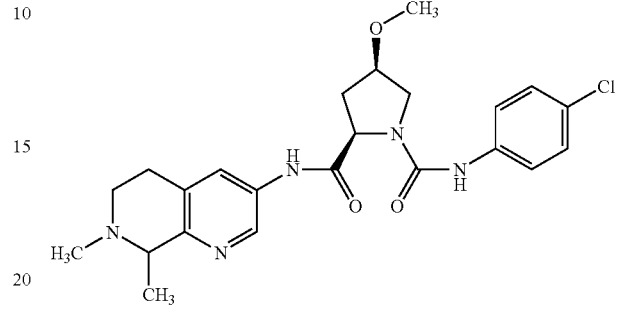

1,2-dimethyl-6-amino-1,2,3,4-tetrahydro-8-aza-isoquinoline was prepared analogously to Example 52a from 1-methyl-3,5-dinitro-pyridone and 1-butoxycarbonyl-piperidin-2-methyl-3-one, subsequent butoxycarbonyl cleaving with TFA, Leukart-Wallach reaction according to Example 11b and reduction of the nitro group analogously to Example 52b and reacted according to Example 14d to form the title compound.

$R_f$ value: 1.07 min (Method B)
$C_{22}H_{28}ClN_5O_3$ (457.96)×$CF_3CO_2H$
Mass spectrum: $(M+H)^+$=458/460 (chlorine isotopes)

Example 56

(2R,4R)-4-methoxy-pyrrolidine-1,2-dicarboxylic acid-1-[(4-chloro-phenyl)-amide]-2-[(2-methyl-1,2,3,4-tetrahydro-8-methoxycarbonyl-isoquinolin-6-yl)-amide (a) 2-methyl-1,2,3,4-tetrahydro-8-methoxycarbonyl-isoquinoline 2-butoxycarbonyl-1,2,3,4-tetrahydro-8-methoxycarbonyl-isoquinoline is deprotected with methanolic HCl and then methylated according to Example 11b.

$R_f$ value: 0.84 min (Method B)
Mass spectrum: $(M+H)^+$=206

(b) 2-methyl-6-nitro-1,2,3,4-tetrahydro-8-methoxy-carbonyl-isoquinoline and regioisomers A mixture of 1.04 g (5.0 mmol) 2-methyl-1,2,3,4-tetrahydro-8-methoxycarbonyl-isoquinoline and sulphuric acid is slowly combined at −7° C. with 0.57 g of potassium nitrate, then stirred for 15 min at −7° C. and for 1 h at ambient temperature. Then it is slowly poured onto ice water and made alkaline with NaOH. The crystals precipitated are filtered off and dried. A mixture of regioisomers is obtained.

$R_f$ value: 0.87 min (Method B)
Mass spectrum: $(M+H)^+=251$

(c) (2R,4R)-4-methoxy-pyrrolidine-1,2-dicarboxylic acid-1-[(4-chloro-phenyl)-amide]-2-[(2-methyl-1,2,3,4-tetrahydro-8-methoxycarbonyl-isoquinolin-6-yl)-amide The title compound is obtained from 2-methyl-6-nitro-1,2,3,4-tetrahydro-8-methoxycarbonyl-isoquinoline (in admixture with regioisomers) by reduction of the nitro group with Pd/charcoal and subsequent amide coupling of 2-methyl-6-amino-1,2,3,4-tetrahydro-8-methoxycarbonyl-isoquinoline according to Example 14d.

$R_f$ value: 1.18 min (Method B)
$C_{25}H_{29}ClN_4O_5$ (500.98)×$CF_3CO_2H$
Mass spectrum: $(M+H)^+=501/503$ (chlorine isotopes)

Example 57

(2R,4R)-4-methoxy-pyrrolidine-1,2-dicarboxylic acid-1-[(4-chloro-phenyl)-amide]-2-[(2-methyl-4-methoxy-1,2,3,4-tetrahydro-isoquinolin-6-yl)-amide (mixture of isomers)

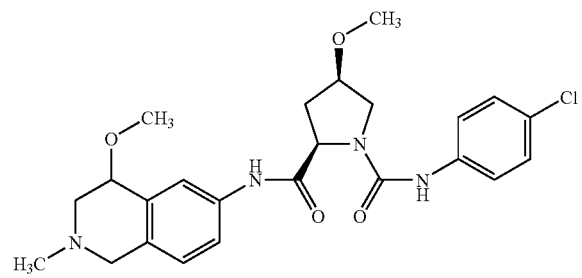

(a) N-methyl-N-(4-nitrophenylmethyl)-2,2-dimethoxy-ethylamine

A mixture of 1.56 g N-methyl-N-(4-nitrobenzyl)amine in 40 ml THF is combined with 2.85 ml of a 45% solution of 2,2-dimethoxyacetaldehyde in tert.-butylmethylether. Then 24 mg of p-TsOH×H2O and 1.12 ml glacial acetic acid are added and the mixture is stirred for 2 h. Then 1.81 g of sodium cyanoborohydride are added batchwise and the mixture is stirred for another 2 h. 5 ml of water are added to the mixture, then it is evaporated down to approx. 30% of the volume, the residue is combined with water and extracted 3× with EtOAc. The combined organic phases are dried with $Na_2SO_4$, concentrated and the crude product is purified by chromatography (Alox; petroleum ether/EtOAc 8/2->7/3).

$R_f$ value: 2.2 min (Method D)
Mass spectrum: $(M+H)^+=255$

(b) 6-nitro-4-methoxy-2-methyl-1,2,3,4-tetrahydro-isoquinoline

A mixture of 0.83 g of N-methyl-N-(4-nitrophenylmethyl)-2,2-dimethoxy-ethylamine and 3.0 ml trifluoromethanesulphonic acid is prepared in a dry ice/ethanol cooling bath, slowly brought to ambient temperature and stirred for 18 h. Then it is poured onto ice water, made alkaline with 2N NaOH, extracted 3× with EtOAc, the organic phases are dried with $Na_2SO_4$, concentrated and purified by repeated chromatography.

$R_f$ value: 1.7 min (Method D)
Mass spectrum: $(M+H)^+=223$

(c) 6-amino-4-methoxy-2-methyl-1,2,3,4-tetrahydro-isoquinoline

A mixture of 70 mg 6-nitro-4-methoxy-2-methyl-1,2,3,4-tetrahydro-isoquinoline, 25 mg Pd/charcoal and 5.0 ml MeOH is hydrogenated for 9 h at 3 bar hydrogen pressure. Then it is filtered and evaporated down.

Yield: quantitative
$R_f$ value: 0.75 (RP-8; methanol/5% NaCl solution=6:4)
Mass spectrum: $(M+H)^+=193$

(d) (2R,4R)-4-methoxy-pyrrolidine-1,2-dicarboxylic acid-1-[(4-chloro-phenyl)-amide]-2-[(2-methyl-4-methoxy-1,2,3,4-tetrahydro-isoquinolin-6-yl)-amide (mixture of isomers)

The title compound is prepared from 6-amino-4-methoxy-2-methyl-1,2,3,4-tetrahydro-isoquinoline and (2R,4R)-1-(4-chloro-phenylcarbamoyl)-4-methoxy-pyrrolidine-2-carboxylic acid according to Example 4e.

$R_f$ value: 2.8 min (Method D)
$C_{24}H_{29}ClN_4O_4$ (472.96)×$HCO_2H$
Mass spectrum: $(M+H)^+=473/475$ (chlorine isotopes)

Example 58

(2R,4R)-4-methoxy-pyrrolidine-1,2-dicarboxylic acid-1-[(4-bromo-phenyl)-amide]-2-[(2-methyl-5,8-difluoro-1,2,3,4-tetrahydro-isoquinolin-7-yl)-amide×HCOOH

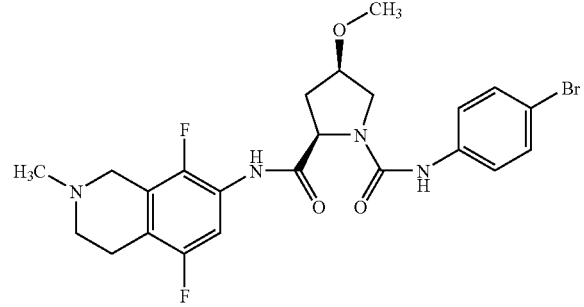

(a) 2-methyl-5,8-difluoro-1,2,3,4-tetrahydro-isoquinoline

The title compound is prepared from 5,8-difluoro-1,2,3,4-tetrahydro-isoquinoline according to Example 11b.

$R_f$ value: 1.6 min (Method D)
Mass spectrum: $(M+H)^+=184$

(b) 2-methyl-5,8-difluoro-7-nitro-1,2,3,4-tetrahydro-isoquinoline

An ice-cooled mixture of 0.94 g (5.1 mmol) 2-methyl-5,8-difluoro-1,2,3,4-tetrahydro-isoquinoline and 2.8 ml conc. $H_2SO_4$ is slowly combined with 0.36 ml 65% nitric acid. Then the mixture is stirred for 2.5 h while cooling with ice and it is then poured onto ice water. It is made alkaline with NaOH, extracted 3× with EtOAc, the organic phases are dried with $Na_2SO_4$, filtered and concentrated.

Mass spectrum: $(M+H)^+ = 229$

(c) (2R,4R)-4-methoxy-pyrrolidine-1,2-dicarboxylic acid-1-[(4-bromo-phenyl)-amide]-2-[(2-methyl-5,8-difluoro-1,2,3,4-tetrahydro-isoquinolin-7-yl)-amide× HCOOH The title compound is reacted from 2-methyl-5,8-difluoro-7-nitro-1,2,3,4-tetrahydro-isoquinoline analogously to synthesis sequence 52b, 14d to form the title compound.

$R_f$ value: 0.25 (silica gel; dichloromethane/ethanol/ammonia=95:5:0.5)

$C_{23}H_{25}BrF_2N_4O_3$ (523.36)×$HCO_2H$

Mass spectrum: $(M+H)^+ = 523/525$ (bromine isotopes)

The following compounds may be prepared analogously to the synthesis steps described above or analogously to methods of synthesis known from the literature, from anilines and proline derivatives known from the literature or obtainable by methods of synthesis known from the literature:

| Ex. | Structural formula | Yield last step | Mass peak(s) | DC/HPLC |
|---|---|---|---|---|
| 17 | (2R,4R)-4-methoxy-pyrrolidine-1,2-dicarboxylic acid-1-[(5-chloro-pyridin-2-yl)-amide]-2-(2,4,4-trimethyl-1,2,3,4-tetrahydro-isoquinolin-7-yl)-amide | 11% | $(M-H)^- =$ 470/472 (chlorine isotopes) | $R_f$ value: 2.65 min Method C |
| 18 | (2R,4R)-4-methoxy-pyrrolidine-1,2-dicarboxylic acid-1-[(4-chloro-phenyl)-amide]-2-(1,2-dimethyl-1,2,3,4-tetrahydro-isoquinolin-7-yl)-amide × $CF_3COOH$, mixture of stereoisomers | 68% | $(M-H)^- =$ 457/459 (chlorine isotopes) | $R_f$ value: 1.12 min Method B |
| 19 | (2R,4R)-4-methoxy-pyrrolidine-1,2-dicarboxylic acid-1-[(5-chloro-pyridin-2-yl)-amide]-2-(1,2-dimethyl-1,2,3,4-tetrahydro-isoquinolin-7-yl)-amide × $CF_3COOH$, mixture of stereoisomers | 33% | $(M+H)^+ =$ 458/460 (chlorine isotopes) | $R_f$ value: 0.99 min Method B |

-continued

| Ex. | Structural formula | Yield last step | Mass peak(s) | DC/HPLC |
|---|---|---|---|---|
| 20 | 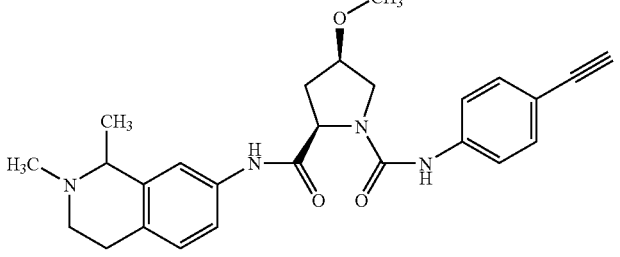<br>(2R,4R)-4-methoxy-pyrrolidine-1,2-dicarboxylate 1-[(4-ethynyl-phenyl)-amide]-2-(1,2-dimethyl-1,2,3,4-tetrahydro-isoquinolin-7-yl)-amide × CF₃COOH, mixture of stereoisomers | 18% | $(M + H)^+ = 447$ | $R_t$ value: 1.11 min Method B |
| 21 | 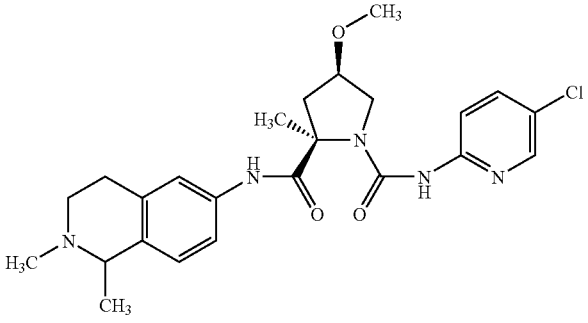<br>(2R,4R)-4-methoxy-2-methyl-pyrrolidine-1,2-dicarboxylic acid-1-[(5-chloro-pyridin-2-yl)-amide]-2-(1,2-dimethyl-1,2,3,4-tetrahydro-isoquinolin-6-yl)-amide × CF₃COOH, mixture of stereoisomers | 5% | $(M + H)^+ =$ 472/474 (chlorine isotopes) | $R_t$ value: 1.11 min Method B |
| 22 | 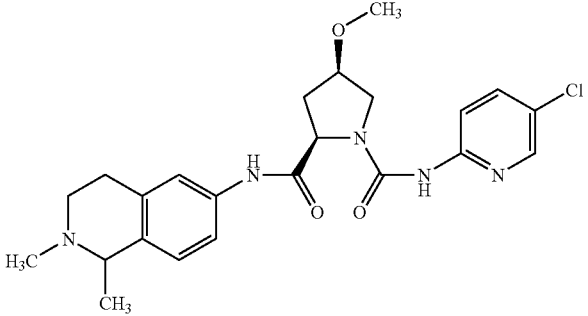<br>(2R,4R)-4-methoxy-pyrrolidine-1,2-dicarboxylic acid-1-[(5-chloro-pyridin-2-yl)-amide]-2-(1,2-dimethyl-1,2,3,4-tetrahydro-isoquinolin-6-yl)-amide × CF₃COOH, mixture of stereoisomers | 4% | $(M + H)^+ =$ 458/460 (chlorine isotopes) | |
| 23 | 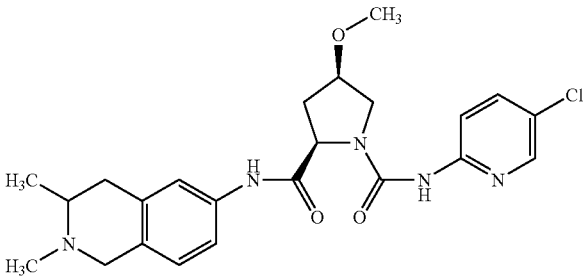<br>(2R,4R)-4-methoxy-pyrrolidine-1,2-dicarboxylic acid-1-[(5-chloro-pyridin-2-yl)-amide]-2-(2,3-dimethyl-1,2,3,4-tetrahydro-isoquinolin-6-yl)-amide, Stereoisomer 1 | 8% | $(M + H)^+ =$ 458/460 (chlorine isotopes) | $R_F$ value: 0.72; silica gel: CH₂Cl₂/ EtOH/ NH₄OH = 80/20/2 |

-continued

| Ex. | Structural formula | Yield last step | Mass peak(s) | DC/HPLC |
|---|---|---|---|---|
| 24 | (2R,4R)-4-methoxy-pyrrolidine-1,2-dicarboxylic acid-1-[(5-bromo-pyridin-2-yl)-amide]-2-(2-methyl-1,2,3,4-tetrahydro-isoquinolin-6-yl)-amide | 18% | $(M + H)^+$ = 488/490 (bromine isotopes) | $R_t$ value: 0.96 min Method B |
| 25 | (2R,4R)-4-methoxy-pyrrolidine-1,2-dicarboxylic acid-1-[(4-bromo-phenyl)-amide]-2-(2-methyl-1,2,3,4-tetrahydro-isoquinolin-6-yl)-amide | 70% | $(M + H)^+$ = 487/489 (bromine isotopes) | $R_t$ value: 1.13 min Method B |
| 26 | (2R)-3,4-dehydropyrrolidine-1,2-dicarboxylic acid-1-[(4-chloro-phenyl)-amide]-2-(2-methyl-1,2,3,4-tetrahydro-isoquinolin-6-yl)-amide × CF$_3$COOH | 54% | $(M + H)^+$ = 411/413 (chlorine isotopes) | $R_t$ value: 1.12 min Method B |
| 27 | (2R,4R)-4-methoxy-pyrrolidine-1,2-dicarboxylate 1-[(4-ethynyl-phenyl)-amide]-2-(2-methyl-1,2,3,4-tetrahydro-isoquinolin-6-yl)-amide × CF$_3$COOH | 16% | $(M + H)^+$ = 433 | $R_t$ value: 1.09 min Method B |

| Ex. | Structural formula | Yield last step | Mass peak(s) | DC/HPLC |
|---|---|---|---|---|
| 28 | 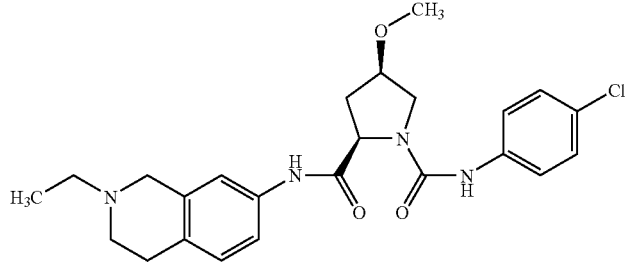<br>(2R,4R)-4-methoxy-pyrrolidine-1,2-dicarboxylic acid-1-[(4-chloro-phenyl)-amide]-2-(2-ethyl-1,2,3,4-tetrahydro-isoquinolin-7-yl)-amide | 25% | $(M + H)^+ =$ 457/459 (chlorine isotopes) | |
| 29 | 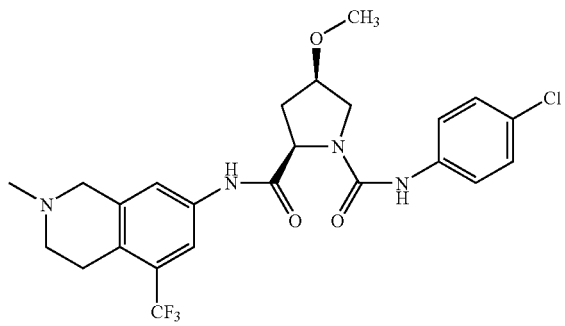<br>(2R,4R)-4-methoxy-pyrrolidine-1,2-dicarboxylic acid-1-[(4-chloro-phenyl)-amide]-2-(2-methyl-5-trifluoromethyl-1,2,3,4-tetrahydro-isoquinolin-7-yl)-amide × HCOOH | 5% | $(M + H)^+ =$ 511/513 (chlorine isotopes) | $R_F$ value: 0.75; silica gel: $CH_2Cl_2$/ EtOH/ $NH_4OH =$ 80/20/2 |
| 30 | 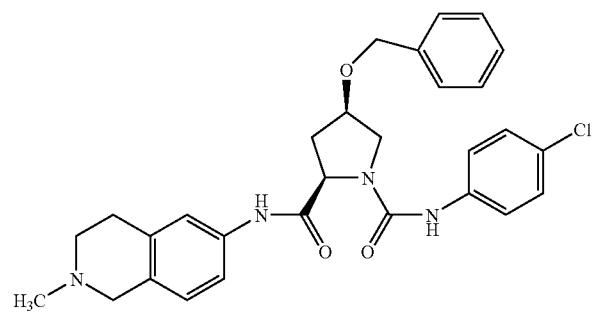<br>(2R,4R)-4-benzyloxy-pyrrolidine-1,2-dicarboxylic acid-1-[(4-chloro-phenyl)-amide]-2-(2-methyl-1,2,3,4-tetrahydro-isoquinolin-6-yl)-amide | 31% | $(M + H)^+ =$ 519/521 (chlorine isotopes) | $R_t$ value: 1.36 min Method B |
| 31 | 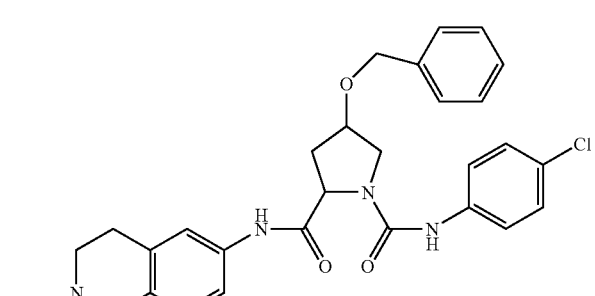<br>4-benzyloxy-pyrrolidine-1,2-dicarboxylic acid-1-[(4-chloro-phenyl)-amide]-2-(2-methyl-1,2,3,4-tetrahydro-isoquinolin-6-yl)-amide, stereoisomer of Ex. 30 | 33% | $(M + H)^+ =$ 519/521 (chlorine isotopes) | $R_t$ value: 1.44 min Method B |

-continued

| Ex. | Structural formula | Yield last step | Mass peak(s) | DC/HPLC |
|---|---|---|---|---|
| 32 | (2R*3aR, 8aR)-octahydro-cyclohepta[b]pyrrol-1,2-dicarboxylic acid-1-[(4-bromo-phenyl)-amide]-2-(2-methyl-1,2,3,4-tetrahydro-isoquinolin-6-yl)-amide | 7% | (M + H)⁺ = 511/513 (bromine isotopes) | $R_t$ value: 1.40 min Method B |
| 33 | (2R,4R)-4-methoxy-pyrrolidine-1,2-dicarboxylic acid-1-phenylamide-2-(2-methyl-1,2,3,4-tetrahydro-isoquinolin-7-yl)-amide × CF₃COOH | 42% | (M + H)⁺ = 409 | $R_t$ value: 1.01 min Method B |
| 34 | (2R,4R)-4-methoxy-2-methyl-pyrrolidine-1,2-dicarboxylic acid-1-[(4-ethynyl-phenyl)-amide]-2-(2-methyl-1,2,3,4-tetrahydro-isoquinolin-6-yl)-amide | 31% | (M + H)⁺ = 447 | $R_t$ value: 1.01 min Method B |
| 35 | (2R)-4-oxo-pyrrolidine-1,2-dicarboxylic acid-1-[(4-chloro-phenyl)-amide]-2-(2-methyl-1,2,3,4-tetrahydro-isoquinolin-6-yl)-amide | 9% | (M + H)⁺ = 427/429 (chlorine isotopes) | $R_t$ value: 1.09 min Method B |

| Ex. | Structural formula | Yield last step | Mass peak(s) | DC/HPLC |
|---|---|---|---|---|
| 36 | (2R)-4-oxo-pyrrolidine-1,2-dicarboxylic acid-1-[(4-bromo-phenyl)-amide]-2-(2-methyl-1,2,3,4-tetrahydro-isoquinolin-6-yl)-amide | 9% | $(M + H)^+$ = 471/473 (bromine isotopes) | $R_t$ value: 1.12 min Method B |
| 37 | (2R)-4,4-dimethyloxy-pyrrolidine-1,2-dicarboxylic acid-1-[(4-chloro-phenyl)-amide]-2-(2-methyl-1,2,3,4-tetrahydro-isoquinolin-6-yl)-amide × $CF_3COOH$ | 3% | $(M + H)^+$ = 473/475 (chlorine isotopes) | $R_t$ value: 1.17 min Method B |
| 38 | (2R)-4,4-dimethyloxy-pyrrolidine-1,2-dicarboxylic acid-1-[(4-bromo-phenyl)-amide]-2-(2-methyl-1,2,3,4-tetrahydro-isoquinolin-6-yl)-amide × $CF_3COOH$ | 5% | $(M + H)^+$ = 517/519 (bromine isotopes) | $R_t$ value: 1.21 min Method B |
| 39 | (8R)-1,4-dioxa-7-aza-spiro[4,4]nonane-7,8-dicarboxylic acid-7-[(4-bromo-phenyl)-amide]-8-(2-methyl-1,2,3,4-tetrahydro-isoquinolin-6-yl)-amide × HCOOH | 31% | $(M + H)^+$ = 515/517 (bromine isotopes) | $R_F$ value: 0.17; silica gel: $CH_2Cl_2$/ EtOH/ $NH_4OH$ = 90/10/1 |

| Ex. | Structural formula | Yield last step | Mass peak(s) | DC/HPLC |
|---|---|---|---|---|
| 40 | (2R,4R)-4-hydroxy-pyrrolidine-1,2-dicarboxylic acid-1-(4-bromophenyl)-amide-2-(2-methyl-1,2,3,4-tetrahydro-isoquinolin-6-yl)-amide | 64% | (M − H)⁻ = 471/473 (bromine isotopes) | $R_f$ value: 0.49 (RP-8; methanol/5% —NaCl solution = 6:4) |
| 41 | (2R,4R)-4-(4-fluorophenyloxy)-pyrrolidine-1,2-dicarboxylic acid-1-(4-chlorophenyl)-amide-2-(2-methyl-1,2,3,4-tetrahydro-isoquinolin-6-yl)-amide × CF₃COOH | 52% | (M + H)⁺ = 523/525 (chlorine isotopes) | $R_t$ value: 1.27 min Method B |
| 42 | (rac)-2-benzyl-pyrrolidine-1,2-dicarboxylic acid-1-(4-bromophenyl)-amide-2-(2-methyl-1,2,3,4-tetrahydro-isoquinolin-6-yl)-amide × HCOOH | 32% | (M + H)⁺ = 545/547 (bromine isotopes) | |
| 43 | 3-aza-bicyclo[3.1.0]hexane-2,3-dicarboxylic acid-3-(4-bromphenyl)amide-2-(2-methyl-1,2,3,4-tetrahydro-isoquinolin-6-yl)amide × HCOOH (mixture of stereoisomers) | 39% | (M + H)⁺ = 469/471 (bromine isotopes) | $R_f$ value: 0.12 (RP-8; methanol/5% NaCl solution = 6:4) |

| Ex. | Structural formula | Yield last step | Mass peak(s) | DC/HPLC |
| --- | --- | --- | --- | --- |
| 44 | (2R,4R)-4-methoxy-2-methyl-pyrrolidine-1,2-dicarboxylic acid-1-[(4-bromo-phenyl)-amide]-2-(2-methyl-1,2,3,4-tetrahydro-isoquinolin-6-yl)-amide × HCOOH | 31% | $(M + H)^+$ = 501/503 (bromine isotopes) | $R_t$ value: 3.0 min Method D |
| 45 | (2R,4R)-4-methoxy-2-methyl-pyrrolidine-1,2-dicarboxylic acid-1-[(3-fluoro-4-bromo-phenyl)-amide]-2-(2-methyl-1,2,3,4-tetrahydro-isoquinolin-6-yl)-amide × HCOOH | 30% | $(M + H)^+$ = 519/521 (bromine isotopes) | $R_t$ value: 3.1 min Method D |
| 46 | (2R,4R)-4-methoxy-2-methyl-pyrrolidine-1,2-dicarboxylic acid-1-[(3-fluoro-4-chloro-phenyl)-amide]-2-(2-methyl-1,2,3,4-tetrahydro-isoquinolin-6-yl)-amide × HCOOH | 25% | $(M + H)^+$ = 475/477 (chlorine isotopes) | $R_t$ value: 3.1 min Method D |
| 47 | (2R,4R)-4-methoxy-pyrrolidine-1,2-dicarboxylic acid-1-[(3-fluoro-4-chloro-phenyl)-amide]-2-(2-methyl-1,2,3,4-tetrahydro-isoquinolin-6-yl)-amide × HCOOH | 42% | $(M + H)^+$ = 461/463 (chlorine isotopes) | $R_F$ value: 0.60; silica gel: $CH_2Cl_2$/EtOH/$NH_4OH$ = 80/20/2 |

| Ex. | Structural formula | Yield last step | Mass peak(s) | DC/HPLC |
|---|---|---|---|---|
| 48 | (2R,4R)-4-methoxy-pyrrolidine-1,2-dicarboxylic acid-1-[(3-fluoro-4-bromo-phenyl)-amide]-2-(2-methyl-1,2,3,4-tetrahydro-isoquinolin-6-yl)-amide × HCOOH | 50% | (M − H)⁻ = 503/505 (bromine isotopes) | R_F value: 0.62; silica gel: CH₂Cl₂/EtOH/NH₄OH = 80/20/2 |
| 49 | (2R,4R)-4-methoxy-pyrrolidine-1,2-dicarboxylic acid-1-[(4-fluoro-phenyl)-amide]-2-(2-methyl-1,2,3,4-tetrahydro-isoquinolin-6-yl)-amide × HCOOH | 61% | (M + H)⁺ = 427 | R_f value: 0.52 (RP-8; methanol/5% —NaCl solution = 6:4) |
| 50 | (2R,4R)-4-methoxy-pyrrolidine-1,2-dicarboxylic acid-1-[(4-bromo-phenyl)-amide]-2-(2-methyl-7-fluoro-1,2,3,4-tetrahydro-isoquinolin-6-yl)-amide × HCOOH | 9% | (M + H)⁺ = 505/507 (bromine isotopes) | R_t value: 3.1 min Method D |
| 51 | (2R,4R)-4-methoxy-pyrrolidine-1,2-dicarboxylic acid-1-(4-chlorophenyl)-amide-2-methyl-2-(2-methyl-1,2,3,4-tetrahydro-isoquinolin-6-yl)-amide × HCOOH | 23% | (M − H)⁻ = 457/459 (chlorine isotopes) | R_t value: 2.67 min Method D |

| Ex. | Structural formula | Yield last step | Mass peak(s) | DC/HPLC |
|---|---|---|---|---|
| 59 | (2R,4R)-4-methoxy-pyrrolidine-1,2-dicarboxylic acid-1-[(4-bromo-phenyl)-amide]-2-(1,1,3-trimethyl-1,2,3,4-tetrahydro-isoquinolin-6-yl)-amide × HCOOH | 32% | (M + H)⁺ = 515/517 (bromine isotopes) | $R_f$ value: 0.42 (RP-8; methanol/5% —NaCl solution = 6:4) |
| 60 | (2R,4R)-4-methoxy-pyrrolidine-1,2-dicarboxylic acid-1-[(4-chloro-phenyl)-amide]-2-(2,2-difluoro-1,2,3,4-tetrahydro-naphthalen-7-yl)-amide | 27% | (M + H)⁺ = 464/466 (chlorine isotopes) | $R_t$ value: 1.64 min Method B |
| 61 | (2R,4R)-4-methoxy-pyrrolidine-1,2-dicarboxylic acid-1-[(4-bromo-phenyl)-amide]-2-(2,4-dimethyl-1,2,3,4-tetrahydro-isoquinolin-6-yl)-amide | | | |
| 62 | (2R,4R)-4-methoxy-pyrrolidine-1,2-dicarboxylic acid-1-[(5-chloro-pyridin-2-yl)-amide]-2-(2,4-dimethyl-1,2,3,4-tetrahydro-isoquinolin-6-yl)-amide | | | |

| Ex. | Structural formula | Yield last step | Mass peak(s) | DC/HPLC |
|---|---|---|---|---|
| 63 | 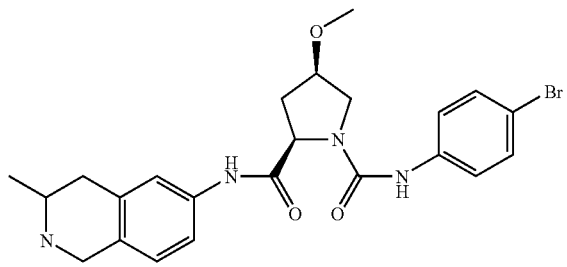<br>(2R,4R)-4-methoxy-pyrrolidine-1,2-dicarboxylic acid-1-[(4-bromo-phenyl)-amide]-2-(3-methyl-1,2,3,4-tetrahydro-isoquinolin-6-yl)-amide | | | |
| 64 | 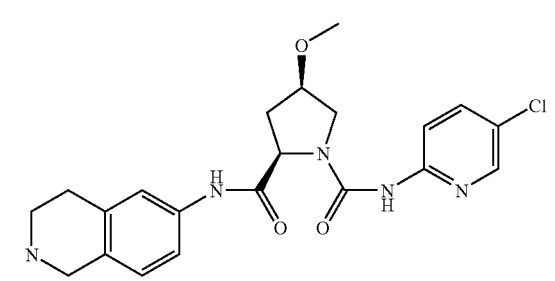<br>(2R,4R)-4-methoxy-pyrrolidine-1,2-dicarboxylic acid-1-[(5-chloro-pyridin-2-yl)-amide]-2-(1,2,3,4-tetrahydro-isoquinolin-6-yl)-amide | | | |
| 65 | 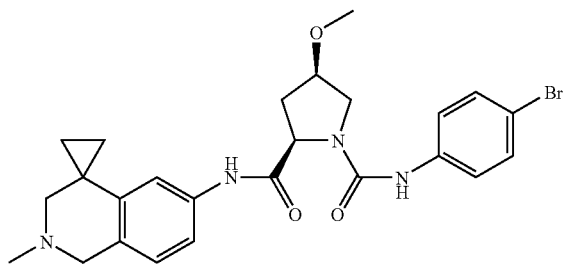 | | | |
| 66 | 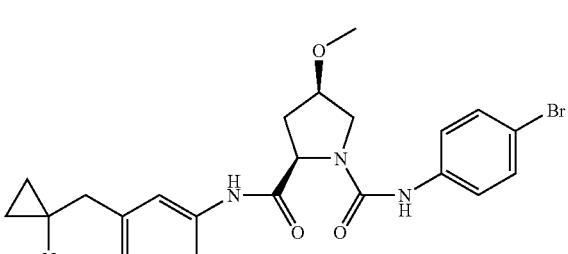 | | | |
| 67 | 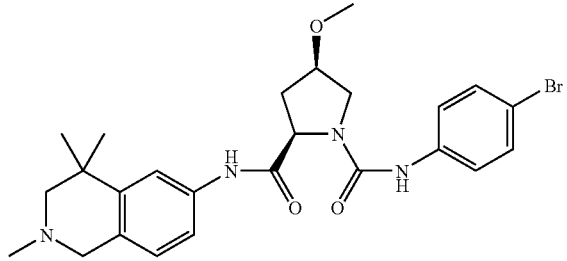 | | | |

| Ex. | Structural formula | Yield last step | Mass peak(s) | DC/HPLC |
|---|---|---|---|---|
| 68 | | | | |
| 69 | | | | |
| 70 | | | | |
| 71 | | | | |
| 72 | | | | |

| Ex. | Structural formula | Yield last step | Mass peak(s) | DC/HPLC |
|---|---|---|---|---|
| 73 | | | | |
| 74 | | | (M + H)⁺ = 587/589 (bromine isotopes) | |
| 75 | | | | |
| 76 | | | | |

The Examples that follow describe the preparation of some pharmaceutical formulations which contain as active substance any desired compound of general formula I:

Example A

Dry ampoule containing 75 mg of active substance per 10 ml

Composition:

| Active substance | 75.0 mg |
|---|---|
| Mannitol | 50.0 mg |
| water for injections | ad 10.0 ml |

Preparation:

Active substance and mannitol are dissolved in water. After packaging the solution is freeze-dried. To produce the solution ready for use for injections, the product is dissolved in water.

Example B

Dry ampoule containing 35 mg of active substance per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use for injections, the product is dissolved in water.

Example C

Tablet containing 50 mg of active substance

Composition:

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

Example D

Tablet containing 350 mg of active substance

Composition:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |

600.0 mg

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

Example E

Capsules containing 50 mg of active substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

Example F

Capsules containing 350 mg of active substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

Example G

Suppositories containing 100 mg of active substance

| Active substance | 100.0 mg |
|---|---|
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylenesorbitan monostearate. At 40° C. the ground active substance is homogeneously dispersed in the melt. It is cooled to 38° C. and poured into slightly chilled suppository moulds.

What is claimed is:

1. A compound of general formula (I)

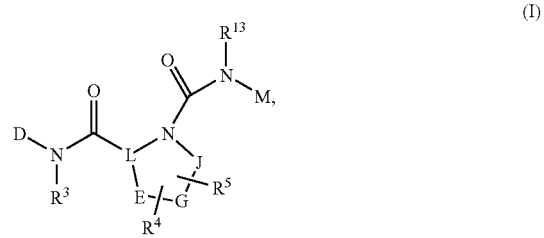

wherein

D denotes a substituted bicyclic ring system of formula

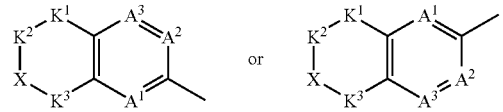

wherein $K^1$ denotes a —$CH_2$—, —$CHR^{7a}$—, —$CR^{7b}R^{7c}$ or a —C(O) group, and wherein $R^{7a}/R^{7b}/R^{7c}$ each independently of one another denote a fluorine atom, a hydroxy, $C_{1-5}$-alkyloxy, a $C_{1-5}$-alkyl group, while the two groups $R^{7b}/R^{7c}$ may not simultaneously be bound to the cyclic carbon atom via a heteroatom, except where —$C(R^{7b}R^{7c})$ corresponds to a —$CF_2$ group, or two groups $R^{7b}/R^{7c}$ together with the cyclic carbon atom may form a 3-membered carbocyclic group and $K^2$ and $K^3$ each independently of one another denote a —$CH_2$—, —$CHR^{8a}$—, —$CR^{8b}R^{8c}$ or a —C(O)— group, wherein $R^{8a}/R^{8b}/R^{8c}$ each independently of one another denote a $C_{1-5}$-alkyl group, or two groups $R^{8b}/R^{8c}$ together with the cyclic carbon atom may form a 3-membered saturated carbocyclic group and in all not more than four groups selected from among $R^{7a}$, $R^{7b}$, $R^{7c}$, $R^{8a}$, $R^{8b}$ and $R^{8c}$ may be present, and X denotes an oxygen or sulphur atom, a sulphene, sulphone, —$CF_2$— or an $NR^1$ group, wherein $R^1$ denotes a hydrogen atom or a hydroxy, $C_{1-3}$-alkyloxy, amino, $C_{1-3}$-alkylamino, di-($C_{1-3}$-alkyl)-amino, a $C_{1-5}$-alkyl, $C_{2-5}$-alkenyl-$CH_2$, $C_{2-5}$-alkynyl-$CH_2$ or a $C_{3-6}$-cycloalkyl group, and wherein $A^1$ denotes either N or $CR^{10}$ $A^2$ denotes either N or $CR^{11}$ $A^3$ denotes either N or $CR^{12}$ wherein $R^{10}$, $R^{11}$ and $R^{12}$ each independently of one another denote a hydrogen, fluorine, chlorine, bromine or iodine atom, or a $C_{1-5}$-alkyl, $CF_3$, a cyano, carboxy, $C_{1-5}$-alkyloxycarbonyl, hydroxy, $C_{1-3}$-alkyloxy, $CF_3O$, $CHF_2O$, $CH_2FO$, amino, $C_{1-5}$-alkylamino, di-($C_{1-5}$-alkyl)-amino or $C_{4-7}$-cycloalkyleneimino group, and -L-E-G-J- denotes a C—C—C—C or —C—C=C—C group which may be substituted by $R^4$ and $R^5$, and $R^3$ denotes a hydrogen atom or a $C_{1-3}$-alkyl group, and $R^4$ denotes a hydrogen atom or a straight-chain or branched $C_{1-6}$-alkyl, $C_{2-6}$-alkenyl or $C_{2-6}$-alkynyl group, wherein the hydrogen atoms of the methylene and/or methyl fragments of the straight-chain or branched $C_{1-6}$-alkyl, $C_{2-6}$-alkenyl or $C_{2-6}$-alkynyl group may optionally be wholly or partly replaced by fluorine atoms, or wherein the hydrogen atoms of the methylene and/or methyl fragments of the straight-chain or branched $C_{1-6}$-alkyl, $C_{2-6}$-alkenyl or $C_{2-6}$-alkynyl group may optionally each be substituted independently of one another by one to two substituents selected from among a $C_{3-5}$-cycloalkyl group, a nitrile, hydroxy or $C_{1-5}$-alkyloxy group, while the hydrogen atoms of the $C_{1-5}$-alkyloxy group may optionally be wholly or partly replaced by fluorine atoms, an allyloxy, propargyloxy, benzyloxy, $C_{1-5}$-alkylcarbonyloxy, $C_{1-5}$-alkyloxycarbonyloxy, carboxy-$C_{1-5}$-alkyloxy, $C_{1-5}$-alkyloxycarbonyl-$C_{1-5}$-alkyloxy, mercapto, $C_{1-5}$-alkylsulphanyl, $C_{1-5}$-alkylsulphinyl, $C_{1-5}$-alkylsulphonyl, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, aminosulphonyl, $C_{1-5}$-alkylaminosulphonyl, di-($C_{1-5}$-alkyl)-aminosulphonyl, $C_{4-7}$-cycloalkyleneiminosulphonyl, amino, $C_{1-5}$-alkylamino, di-($C_{1-5}$-alkyl)-amino, $C_{1-5}$-alkylcarbonylamino, $C_{1-5}$-alkyl-sulphonylamino, N—($C_{1-5}$-alkylsulphonyl)-$C_{1-5}$-alkylamino, $C_{3-6}$-cycloalkylcarbonyl-amino group, or a morpholinyl, thiomorpholinyl, pyrrolidinyl, piperidinyl, piperazinyl, tetrahydrofuranyl, tetrahydropyranyl group, while the above-mentioned carbocyclic and heterocyclic groups in the ring may each be substituted by 1-4 $C_{1-3}$-alkyl or $C_{1-3}$-alkylcarbonyl groups or by 1-2 oxo groups, or wherein the hydrogen atoms of the $sp^2$-hybridised carbon atoms of the straight-chain or branched $C_{2-6}$-alkenyl group may optionally be wholly or partly replaced by fluorine atoms, or $R^4$ denotes a nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group wherein optionally a methylene group may be replaced by a oxygen, sulphur or $C_{0-3}$-alkyl-substituted nitrogen atom, or $R^4$ denotes a phenyl, mono- or bicyclic heteroaryl, phenyl-$C_{1-5}$-alkyl or mono- or bicyclic heteroaryl-$C_{1-5}$-alkyl group, which may optionally be mono- to trisubstituted in the phenyl or heteroaryl moiety by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy and $C_{1-5}$-alkyloxycarbonyl group, and if -L-E-G-J- denotes a —C—C—C—C group, $R^4$ at E or G may also denote a fluorine atom or a hydroxy, methoxy, $C_{3-5}$-alkenyl-oxy, $C_{3-5}$-alkynyloxy, $C_{2-5}$-alkyloxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-3}$-alkyloxy, heteroaryl-$C_{0-3}$-alkyloxy, amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonyl-amino group, while the methyl or methylene groups present in the above-mentioned alkyl or cycloalkyl groups may each independently of one another be substituted by a substituent selected from among morpholinyl, thiomorpholinyl, pyrrolidinyl, piperidinyl, piperazinyl, tetrahydrofuranyl, tetrahydropyranyl, dimethylaminocarbonyl, $C_{1-5}$-alkyloxycarbonyl, carboxy, methyl, hydroxy, methoxy or amino, and the above-mentioned phenyl or heteroaryl groups may optionally be mono- to trisubstituted by identical or different substituents selected from among fluorine, chlorine, bromine and iodine atoms, and $C_{1-5}$-alkyl, trifluoromethyl, amino, $C_{1-5}$-alkyl-amino, di-($C_{1-5}$-alkyl)-amino, hydroxy, $C_{1-5}$-alkyloxy, mono-, di- or trifluoromethoxy, carboxy- and $C_{1-5}$-alkyloxycarbonyl group, with the proviso that two heteroatoms selected from among oxygen and nitrogen are separated from one another by precisely one optionally substituted $CH_2$ group or that two atoms form an —O—O or —S—O— bond is excluded, and $R^5$ denotes a hydrogen atom, a $C_{1-5}$ alkyl, $C_{2-5}$ alkenyl or $C_{2-5}$ alkynyl or a phenyl-$C_{0-5}$ alkyl group, wherein the alkyl group may be substituted by a hydroxy, methoxy, hydroxycarbonyl or $C_{1-5}$-alkoxycarbonyl group, or if $R^5$ is linked to E or G it may also denote a hydroxy or methoxy group, or $R^4$ and $R^5$, if they are bound to the same carbon atom, they may form together with the carbon atom a —C=O group or a —$CF_2$— group, or $R^4$ and $R^5$, if they are bound to the same carbon atom or to two adjacent carbon atoms, together with the carbon atom(s) they may form a 3-7-membered carbocyclic group or a monounsaturated 5-7 membered carbocyclic group, wherein one of the carbon chain members of this cyclic group may be replaced by an oxygen or sulphur atom or a —NH, —N($C_{1-5}$-alkyl), —N($C_{1-4}$-alkylcarbonyl) or a carbonyl, sulphinyl or sulphonyl group, or two directly adjacent carbon chain members of these $C_{4-7}$-carbocyclic groups may together be replaced by a —C(O)NH, —C(O)N($C_{1-5}$-alkyl), —S(O)$_2$NH, or —S(O)$_2$N($C_{1-5}$-alkyl) group, or four directly adjacent carbon chain members of these $C_{5-7}$-carbocyclic groups may together be replaced by an —O—CH$_2$—CH$_2$—O group, or 1 to 3 carbon atoms of these 3-7-membered cyclic groups may optionally be substituted independently of one another by in each case one or two fluorine atoms or one or two $C_{1-5}$-alkyl groups or a hydroxy, formyloxy, $C_{1-5}$-alkyloxy, $C_{1-5}$-alkylcarbonyloxy, amino, $C_{1-5}$-alkylamino, di-($C_{1-5}$-alkyl)-amino, $C_{4-7}$-cycloalkyleneimino, $C_{1-5}$-alkylcarbonylamino, $C_{3-6}$-cycloalkylcarbonylamino, nitrile, carboxy-$C_{1-5}$-alkyl, $C_{1-5}$-alkyloxycarbonyl-$C_{1-5}$-alkyl, carboxy, $C_{1-5}$-alkyloxycarbonyl, aminocarbonyl, $C_{1-5}$-alkylaminocarbonyl, di-($C_{1-5}$-alkyl)-aminocarbonyl or $C_{4-7}$-cycloalkyleneiminocarbonyl group, with the proviso that a cyclic group of this kind formed from $R^4$ and $R^5$ together, wherein two nitrogen atoms or one nitrogen and one oxygen atom in the cyclic group are separated from one another by precisely one optionally substituted CH$_2$ group, or wherein two atoms in the ring form a —O—O or —S—O— bond is excluded, or the fragment

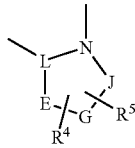

denotes the group

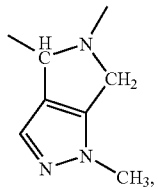

$R^{13}$ denotes a hydrogen atom or a $C_{1-5}$ alkyl group,

M denotes a phenyl, thienyl or pyridyl ring optionally substituted by $R^2$ and $R^6$, wherein $R^2$ denotes a fluorine, chlorine, bromine or iodine atom or a methyl, ethyl, vinyl, methoxy, ethynyl, cyano or —C(O)NH$_2$ group, and $R^6$ denotes a hydrogen, fluorine, chlorine, bromine or iodine atom or a hydroxy, methoxy, trifluoromethoxy, a $C_{1-3}$-alkyl optionally substituted by fluorine atoms, a cyano, amino or NH$_2$C(O) group, while, unless stated otherwise, by the term "heteroaryl group" mentioned hereinbefore in the definitions is meant a monocyclic 5- or 6-membered heteroaryl group, wherein the 6-membered heteroaryl group contains one, two or three nitrogen atoms, and the 5-membered heteroaryl group contains an imino group optionally substituted by a $C_{1-3}$-alkyl group, or an oxygen or sulphur atom, or an imino group optionally substituted by a $C_{1-3}$-alkyl group or an oxygen or sulphur atom and additionally one or two nitrogen atoms, or an imino group optionally substituted by a $C_{1-3}$-alkyl group and three nitrogen atoms, and moreover a phenyl ring optionally substituted by a fluorine, chlorine or bromine atom, a $C_{1-3}$-alkyl, hydroxy, $C_{1-3}$-alkyloxy group, amino, $C_{1-3}$-alkylamino, di-($C_{1-3}$-alkyl)-amino or $C_{3-6}$-cycloalkyleneimino group may be fused to the above-mentioned monocyclic heteroaryl groups via two adjacent carbon atoms, and the bond is effected via a nitrogen atom or a carbon atom of the heterocyclic moiety or a fused-on phenyl ring, and wherein, unless stated otherwise, by the term "halogen atom" mentioned hereinbefore in the definitions is meant an atom selected from among fluorine, chlorine, bromine and iodine, and wherein the alkyl, alkenyl, alkynyl and alkyloxy groups contained in the previously mentioned definitions which have more than two carbon atoms may, unless stated otherwise, be straight-chain or branched and the alkyl groups in the previously mentioned dialkylated groups may be identical or different, and the hydrogen atoms of the methyl or ethyl groups contained in the foregoing definitions, unless stated otherwise, may be wholly or partly replaced by fluorine atoms, the tautomers, the enantiomers, the diastereomers, the mixtures, and the salts thereof.

2. The compound of general formula (I) according to claim 1, wherein

X denotes an NR$^1$ group, wherein R$^1$ denotes a hydrogen atom or a $C_{1-5}$-alkyl, allyl or cyclopropyl group, and $A^1$ denotes CR$^{10}$, $A^2$ denotes CR$^{11}$, $A^3$ denotes either N or CR$^{12}$, wherein R$^{10}$, R$^{11}$ and R$^{12}$ each independently of one another denote a hydrogen, fluorine or chlorine atom, or a methyl, CF$_3$, cyano, carboxy, $C_{1-5}$-alkyloxycarbonyl, hydroxy, methoxy, CF$_3$O, CHF$_2$O, CH$_2$FO group, the tautomers, the enantiomers, the diastereomers, the mixtures, and the salts thereof.

3. The compound of general formula (I) according to claim 1, wherein $R^4$ denotes a hydrogen atom or a straight-chain or branched $C_{1-6}$-alkyl group, wherein the hydrogen atoms of the methylene and/or methyl fragments of the straight-chain or branched $C_{1-6}$-alkyl group may optionally be wholly or partly replaced by fluorine atoms, or wherein the hydrogen atoms of the methylene and/or methyl fragments of the straight-chain or branched $C_{1-6}$-alkyl group may optionally each be substituted independently of one another by a substituent selected from among a hydroxy, $C_{1-5}$-alkyloxy, carboxy, $C_{1-5}$-alkyloxycarbonyl, aminocarbonyl, $C_{1-5}$-alkylaminocarbonyl, di-($C_{1-5}$-alkyl)-aminocarbonyl, $C_{4-7}$-cycloalkyleneiminocarbonyl, amino, $C_{1-5}$-alkylamino, di-($C_{1-5}$-alkyl)-amino, $C_{1-5}$-alkylcarbonylamino, $C_{1-5}$-alkylsulphonylamino, N—($C_{1-5}$-alkylsulphonyl)-$C_{1-5}$-alkylamino, $C_{3-6}$-cycloalkylcarbonylamino group, or $R^4$ denotes a nitrile, carboxy, aminocarbonyl, $C_{1-5}$-alkylaminocarbonyl, $C_{3-6}$-cycloalkylaminocarbonyl, di-($C_{1-5}$-alkyl)-aminocarbonyl, $C_{1-5}$-alkyloxycarbonyl or a $C_{4-7}$-cycloalkyleneiminocarbonyl group wherein a methylene group may optionally be replaced by a oxygen, sulphur or $C_{0-3}$-alkyl-substituted nitrogen atom, and if -L-E-G-J- denotes a —C—C—C—C group, $R^4$ at E or G may also denote a fluorine atom or a hydroxy, methoxy, $C_{3-5}$-alkenyloxy, $C_{3-5}$-alkynyloxy, $C_{2-5}$-alkyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy, phenyl-$C_{0-2}$-alkyloxy group, which may be substituted in the phenyl ring by 1-2 fluorine atoms or methoxy groups, an amino, $C_{1-5}$-alkylamino, di-($C_{1-5}$-alkyl)-amino, $C_{4-7}$-cycloalkyleneimino, $C_{1-3}$-acylamino, ($C_{1-3}$-acyl)$C_{1-3}$-alkylamino, $C_{1-5}$-alkyloxycarbonylamino, $C_{1-5}$-alkylaminocarbonylamino, di($C_{1-5}$-alkyl)aminocarbonylamino or a $C_{4-7}$-cycloalkyleneiminocarbonylamino group, while the methyl or methylene groups present in the above-mentioned alkyl or cycloalkyl groups may each independently of one another be substituted by a substituent selected from among dimethylaminocarbonyl, $C_{1-5}$alkyloxycarbonyl, carboxy, methyl, hydroxy, methoxy or amino, with the proviso that two heteroatoms selected from among oxygen and nitrogen are separated from one another by precisely one optionally substituted $CH_2$ group, or that two atoms form an —O—O or —S—O— bond is excluded, and $R^5$ denotes a hydrogen atom or a $C_{1-5}$ alkyl, allyl, propargyl or benzyl group, or if $R^5$ is linked to E or G, it may also denote a hydroxy or methoxy group or $R^4$ and $R^5$ if they are bound to the same carbon atom, may form together with the carbon atom a —C=O group, or a —$CF_2$— group, or $R^4$ and $R^5$ if they are bound to the same carbon atom or to two adjacent carbon atoms, may form together with the carbon atom(s) a 3-7-membered carbocyclic group, while one of the carbon chain members of this cyclic group may be replaced by an oxygen or sulphur atom or a —NH—, —N($C_{1-5}$-alkyl), —N($C_{1-4}$-alkylcarbonyl) or a carbonyl, sulphinyl or sulphonyl group, or two directly adjacent carbon chain members of these $C_{4-7}$-carbocyclic groups may together be replaced by an —C(O)NH, —C(O)N($C_{1-5}$-alkyl), —S(O)$_2$NH, or —S(O)$_2$N($C_{1-5}$-alkyl) group, or four directly adjacent carbon chain members of these $C_{5-7}$-carbocyclic groups may together be replaced by a —O—$CH_2$—$CH_2$O group, with the proviso that a cyclic group formed from $R^4$ and $R^5$ together, wherein two nitrogen atoms or one nitrogen and one oxygen atom in the cyclic group are separated from one another by precisely one optionally substituted $CH_2$ group, or wherein two atoms in the ring form a —O—O or —S—O— bond is excluded, the tautomers, the enantiomers, the diastereomers, the mixtures, and the salts thereof.

4. The compound of general formula (I) according to claim 1, wherein

-L-E-G-J- denotes a —C—C—C—C group that may be substituted by $R^4$ and $R^5$, which are defined as in claim 1, the tautomers, the enantiomers, the diastereomers, the mixtures, and the salts thereof.

5. The compound of general formula (I) according to claim 1, wherein

D denotes a substituted bicyclic ring system of general formula

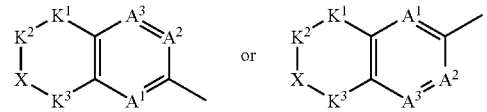

wherein $K^1$ denotes a —$CH_2$, —$CHR^{7a}$, —$CR^{7b}R^{7c}$ or a —C(O) group, wherein $R^{7a}$ denotes a $C_{1-2}$-alkyl group and $R^{7b}$/$R^{7c}$ each independently of one another denote a hydroxy, methoxy or a $C_{1-3}$-alkyl group, while the two groups $R^{7b}$/$R^{7c}$ may not simultaneously be bound to the cyclic carbon atom via an oxygen atom, or two groups $R^{7b}$/$R^{7c}$ together with the cyclic carbon atom may form a 3-membered carbocyclic group, and $K^2$ and $K^3$ in each case independently of one another denote a —$CH_2$, —$CHR^{8a}$ or a —$CR^{8b}R^{8c}$ group, wherein $R^{8a}$/$R^{8b}$/$R^{8c}$ each independently of one another denote a $C_{1-3}$-alkyl group, or two groups $R^{8b}$/$R^{8c}$ together with the cyclic carbon atom may form a 3-membered saturated carbocyclic group, and in all not more than four groups selected from among $R^{7a}$, $R^{7b}$, $R^{7c}$, $R^{8a}$, $R^{8b}$ and $R^{8c}$ may be present, and X denotes a $NR^1$ group, wherein $R^1$ denotes a hydrogen atom or a $C_{1-3}$-alkyl, allyl or cyclopropyl group, and $A^1$ denotes $CR^{10}$, $A^2$ denotes $CR^{11}$, $A^3$ denotes $CR^{12}$, wherein $R^{10}$, $R^{11}$ and $R^{12}$ each independently of one another denote a hydrogen, fluorine or chlorine atom, or a methyl, $CF_3$, hydroxy, methoxy, $CF_3O$, $CHF_2O$, $CH_2FO$ group, and -L-E-G-J- denotes a —C—C—C—C group, which may be substituted by $R^4$ and $R^5$, and $R^3$ denotes a hydrogen atom, and $R^4$ denotes a hydrogen atom or a straight-chain or branched $C_{1-3}$-alkyl group, wherein the hydrogen atoms of the methylene and/or methyl fragments of the straight-chain or branched $C_{1-6}$-alkyl group may optionally be substituted independently of one another by a substituent selected from among a hydroxy, $C_{1-5}$-alkyloxy, carboxy, $C_{1-5}$-alkyloxycarbonyl group, or, if $R^4$ is bound to E or G, it may also denote a fluorine atom or a hydroxy, methoxy, $C_{3-5}$-alkenyl-oxy, $C_{2-5}$-alkyl-oxy, $C_{3-6}$-cycloalkyl-oxy, $C_{1-5}$-alkylaminocarbonyloxy, di($C_{1-5}$-alkyl)aminocarbonyloxy or $C_{4-7}$-cycloalkyleneiminocarbonyloxy group, with the proviso that two heteroatoms selected from among oxygen and nitrogen are separated from one another by precisely one optionally substituted OH2 group is excluded, and $R^5$ denotes a hydrogen atom or a $C_{1-5}$ alkyl, allyl or benzyl group, or if $R^5$ is linked to E or G it may also denote a hydroxy or methoxy group, or $R^4$ and $R^5$ if they are bound to the same carbon atom, may form together with the carbon atom a —C=O group, or a —$CF_2$— group, or R⁴ and R⁵ if they are bound to the same carbon atom or to two adjacent carbon atoms, may form together with the carbon atom(s) a 3-6-membered carbocyclic group, while four directly adjacent carbon chain members of these $C_{5-6}$-carbocyclic groups may together be replaced by an —O—CH₂—CH₂O group, R¹³ denotes a hydrogen atom, M denotes a phenyl substituted by R² in the 4-position or a pyridyl ring substituted by R² in the 5-position, wherein R² denotes a fluorine, chlorine, bromine atom, a methoxy or ethynyl group, and R⁶ denotes a hydrogen or fluorine atom, the tautomers, the enantiomers, the diastereomers, the mixtures, and the salts thereof.

6. The compound of general formula (I) according claim 1, wherein the central ring

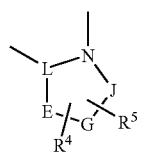

denotes either

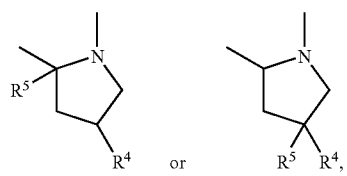

the tautomers, the enantiomers, the diastereomers, the mixtures, and the salts thereof.

7. The compound of general formula (I) according to claim 1, wherein

D denotes a substituted bicyclic ring system of general formula

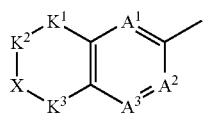

the tautomers, the enantiomers, the diastereomers, the mixtures, and the salts thereof.

8. The compounds of general formula (I) according to claim 1, which are in the R configuration at the chain members G and L of the 5-membered central ring, and the salts thereof.

9. A pharmaceutical composition comprising a compound according to claim 1 and one or more inert carriers or diluents.

10. A method for preparing a pharmaceutical composition comprises the step of formulating a compound according to claim 1 with one or more inert carrier or diluents.

11. A compound according to claim 1, wherein said compound is selected from the group consisting of:

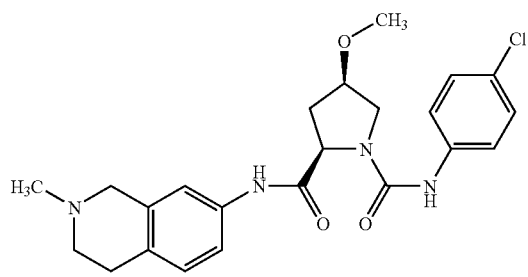

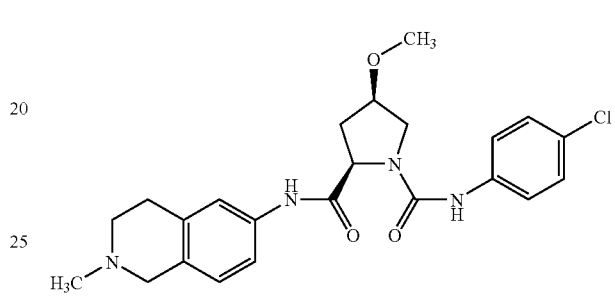

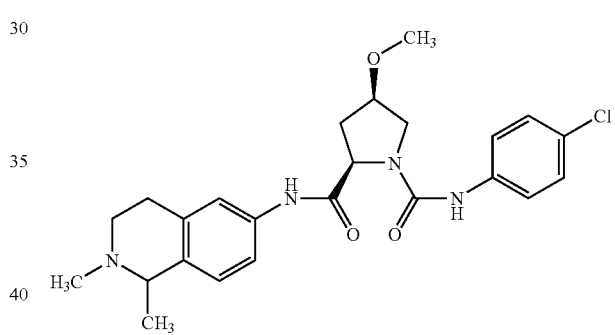

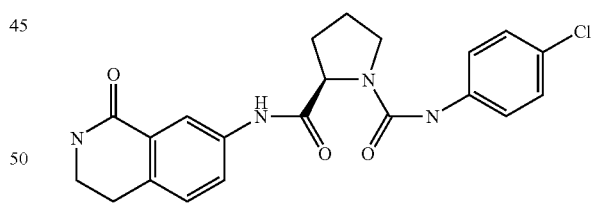

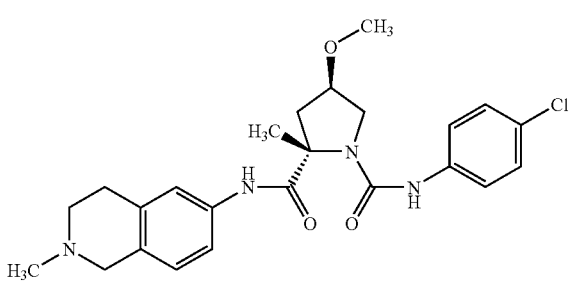

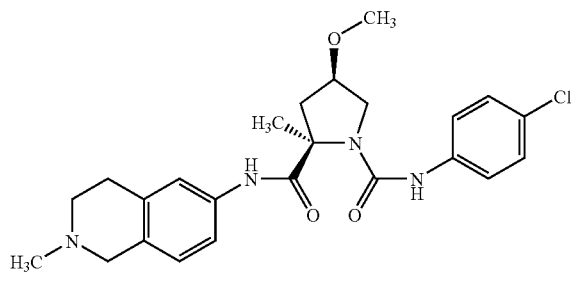
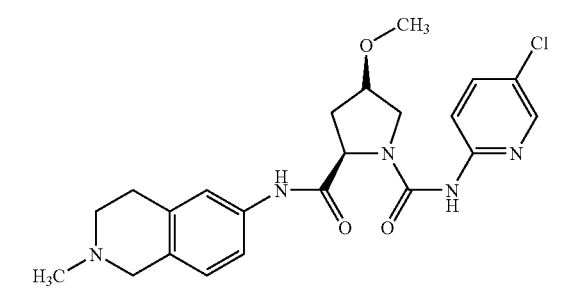
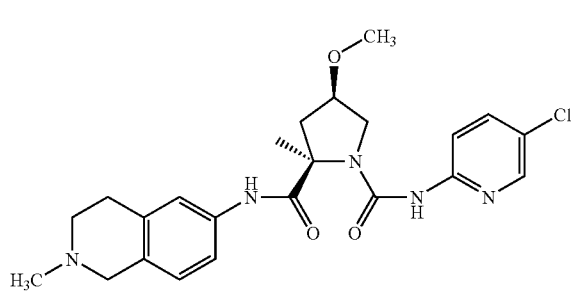
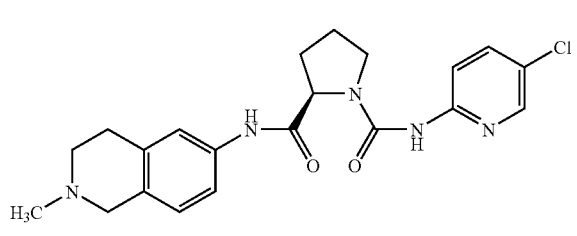
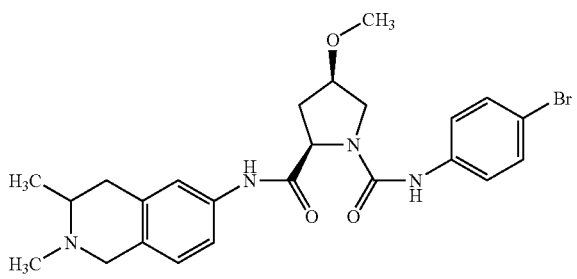
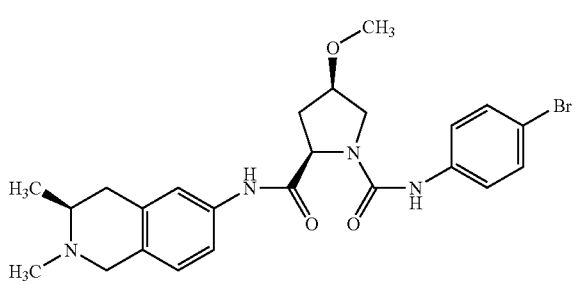
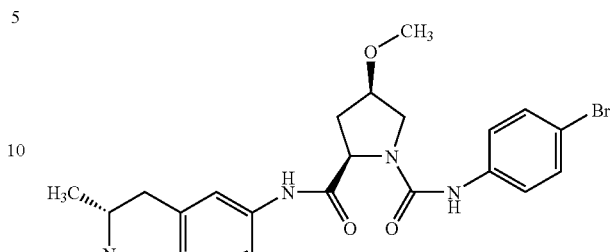
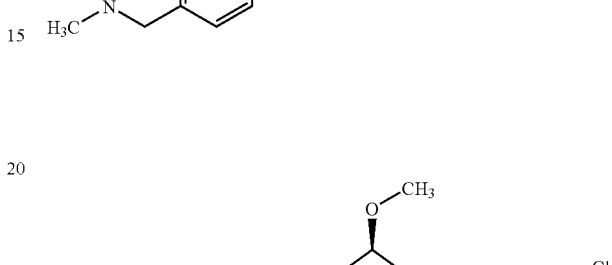
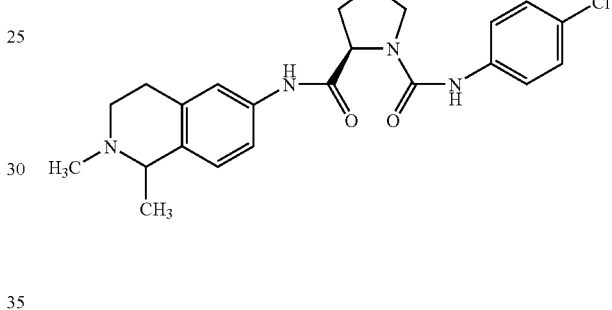
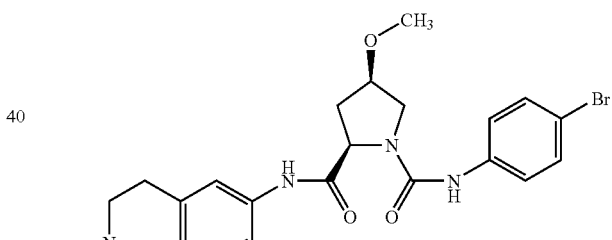
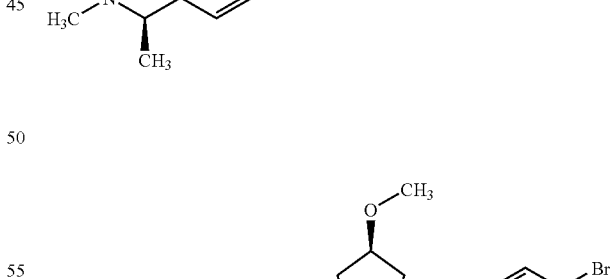
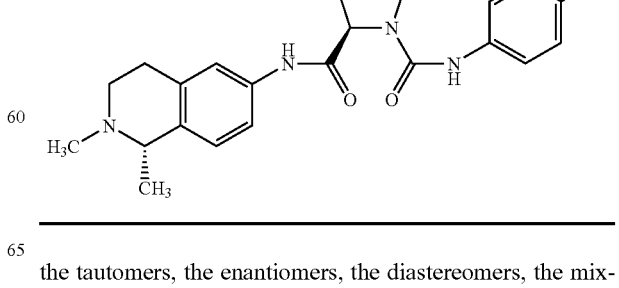
the tautomers, the enantiomers, the diastereomers, the mixtures and the salts thereof.

12. A compound according to claim 1, wherein said compound is selected from the group consisting of:
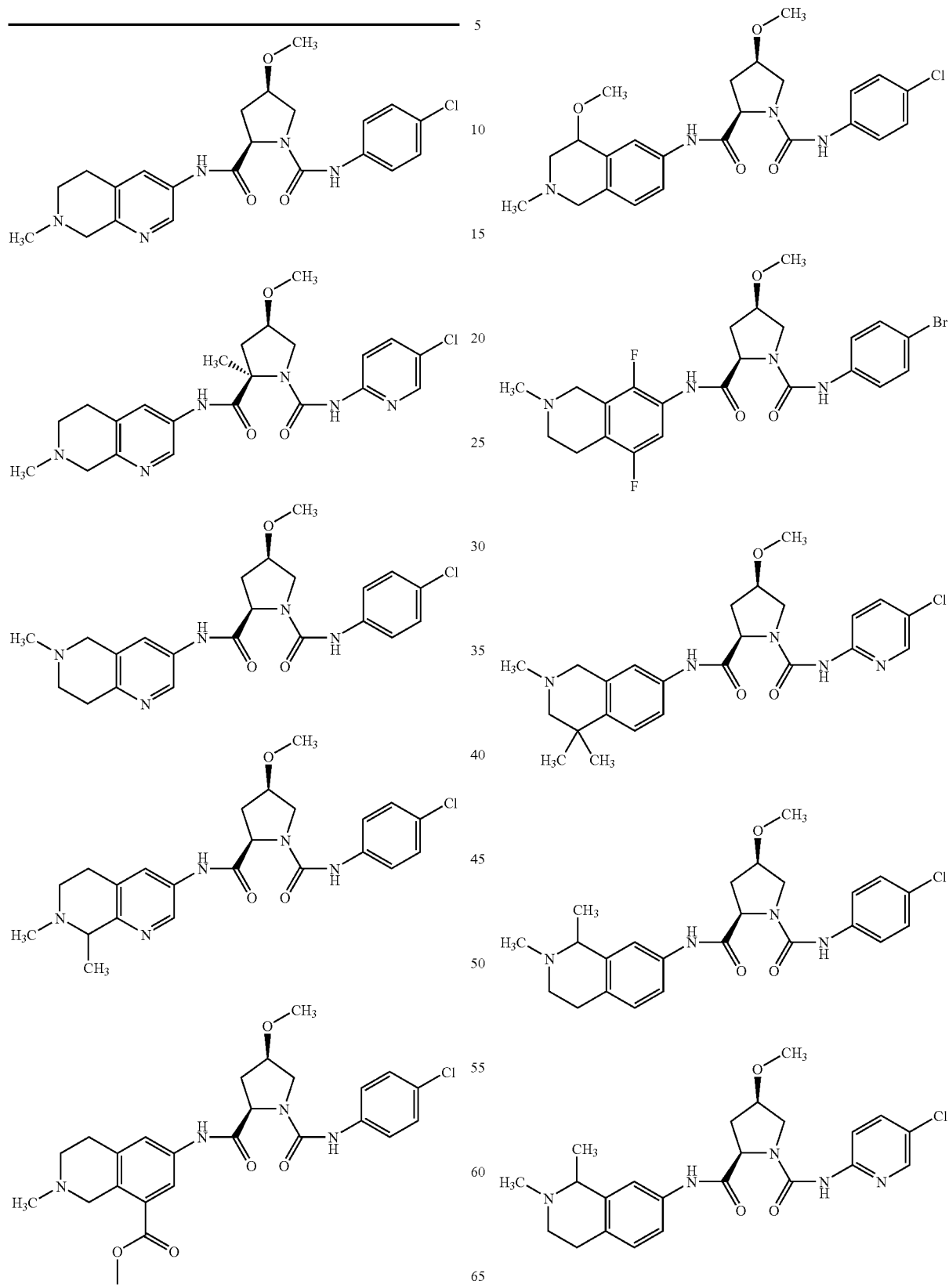

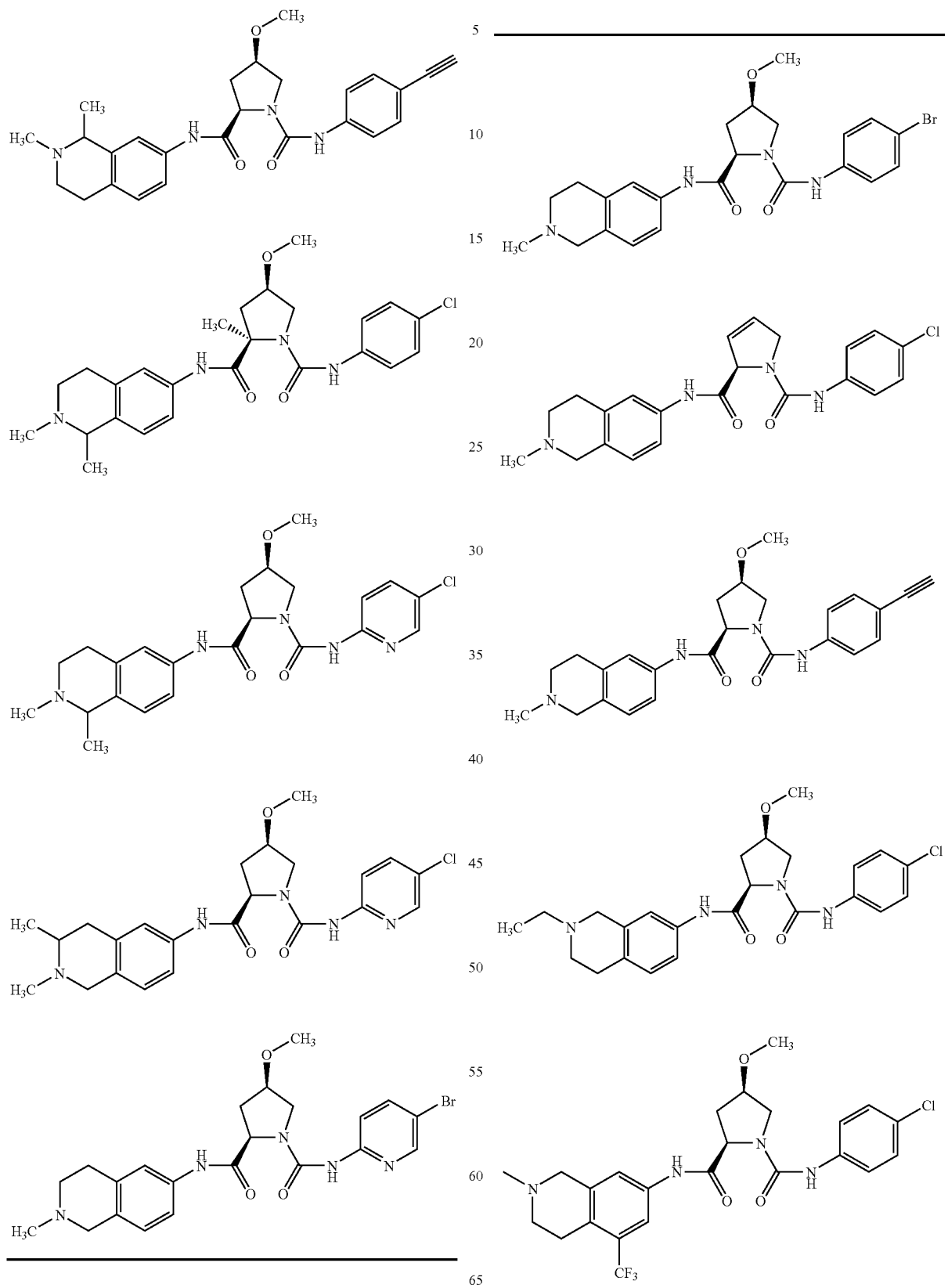
13. A compound according to claim 1, wherein said compound is selected from the group consisting of:
the tautomers, the enantiomers, the diastereomers, the mixtures and the salts thereof.

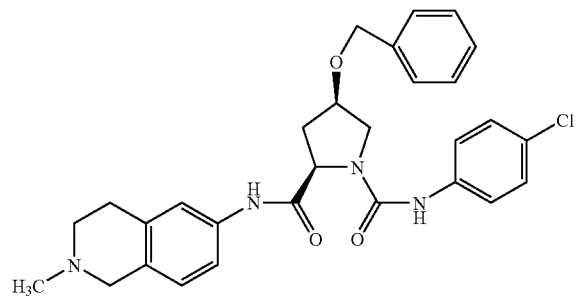
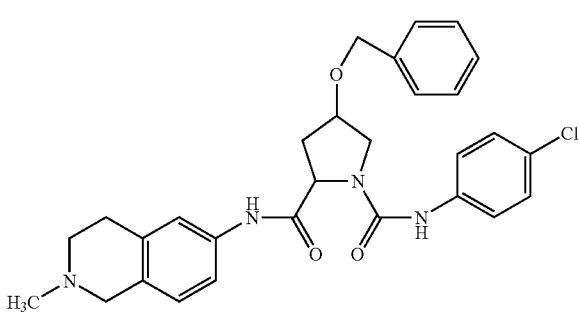
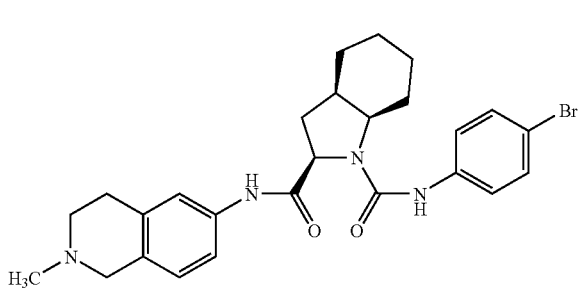
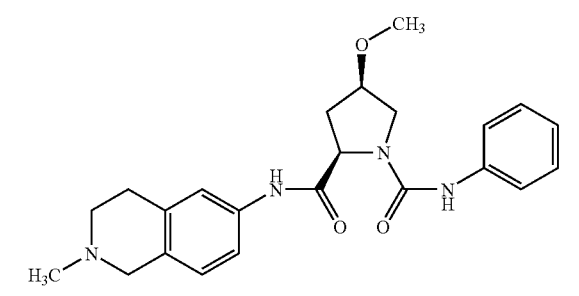
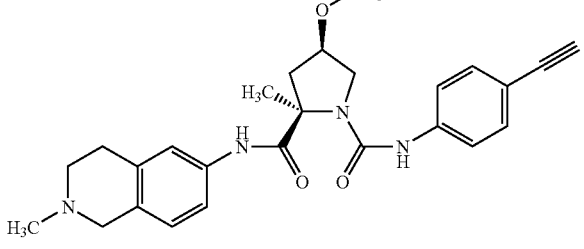
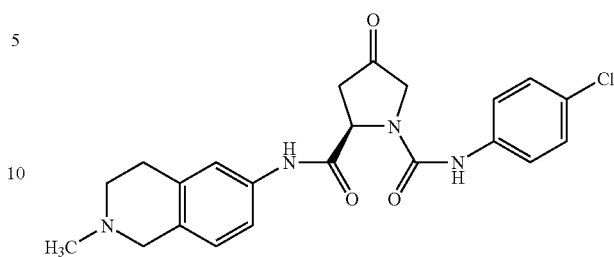
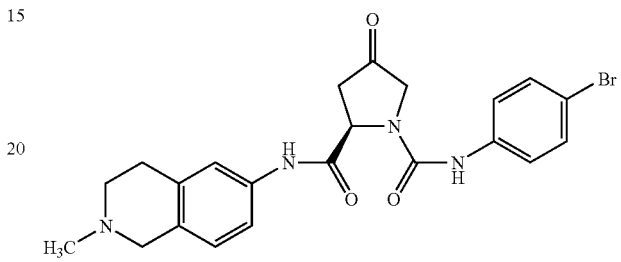
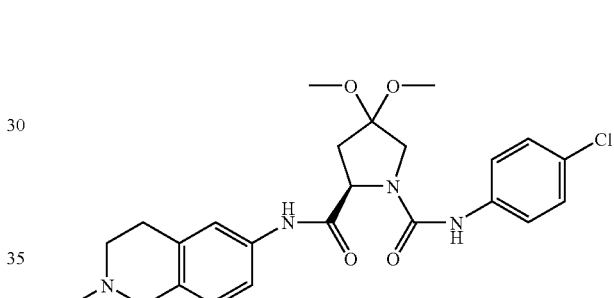
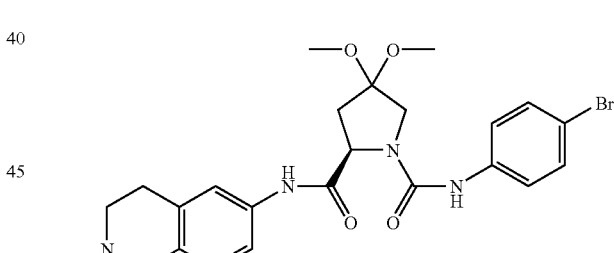
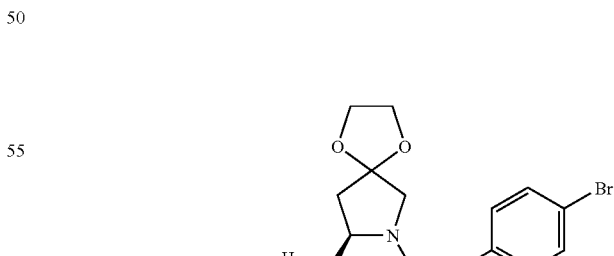
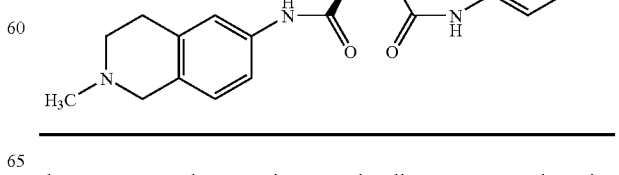
the tautomers, the enantiomers, the diastereomers, the mixtures and the salts thereof.

14. A compound according to claim 1, wherein said compound is selected from the group consisting of:
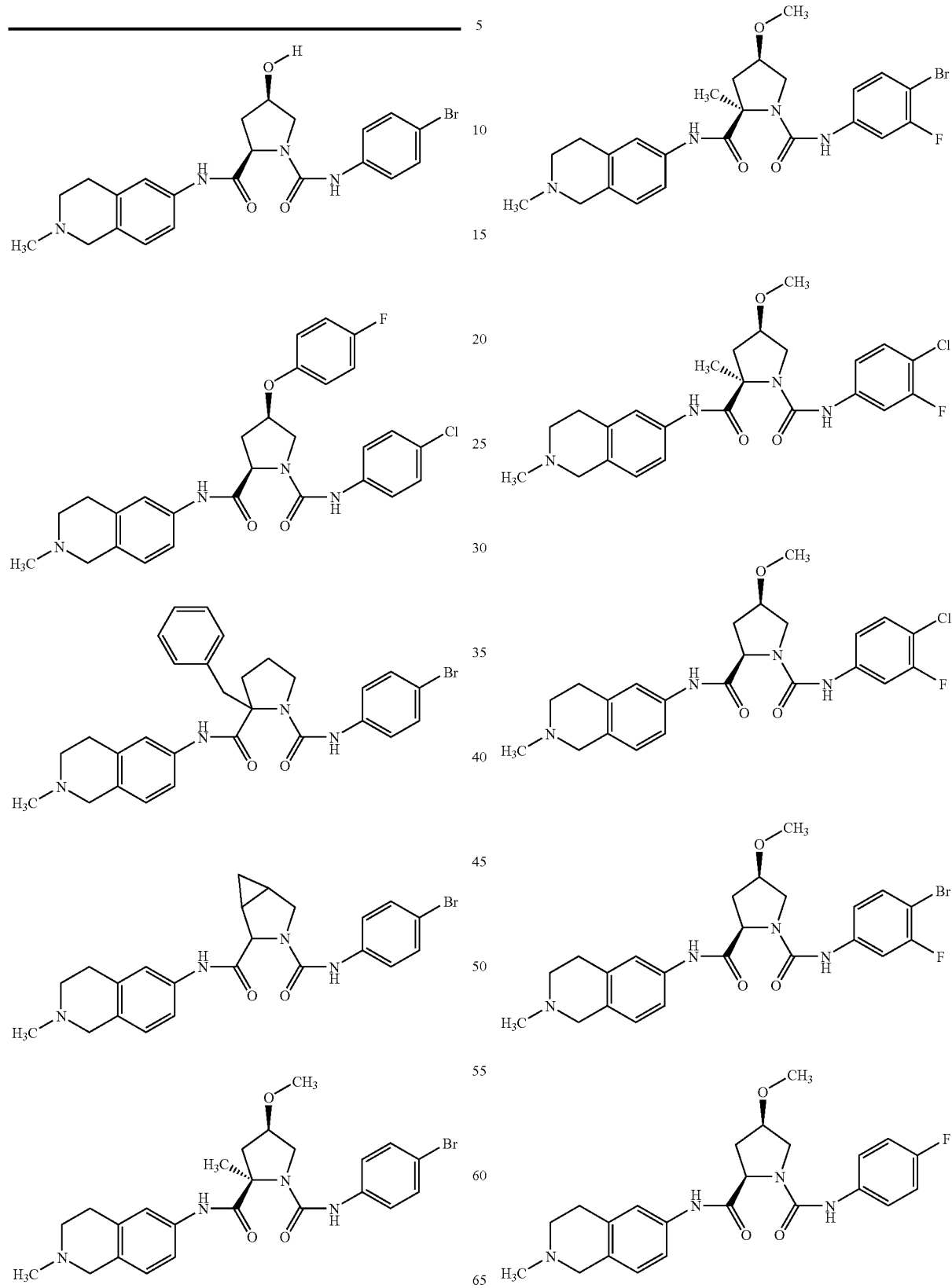

-continued
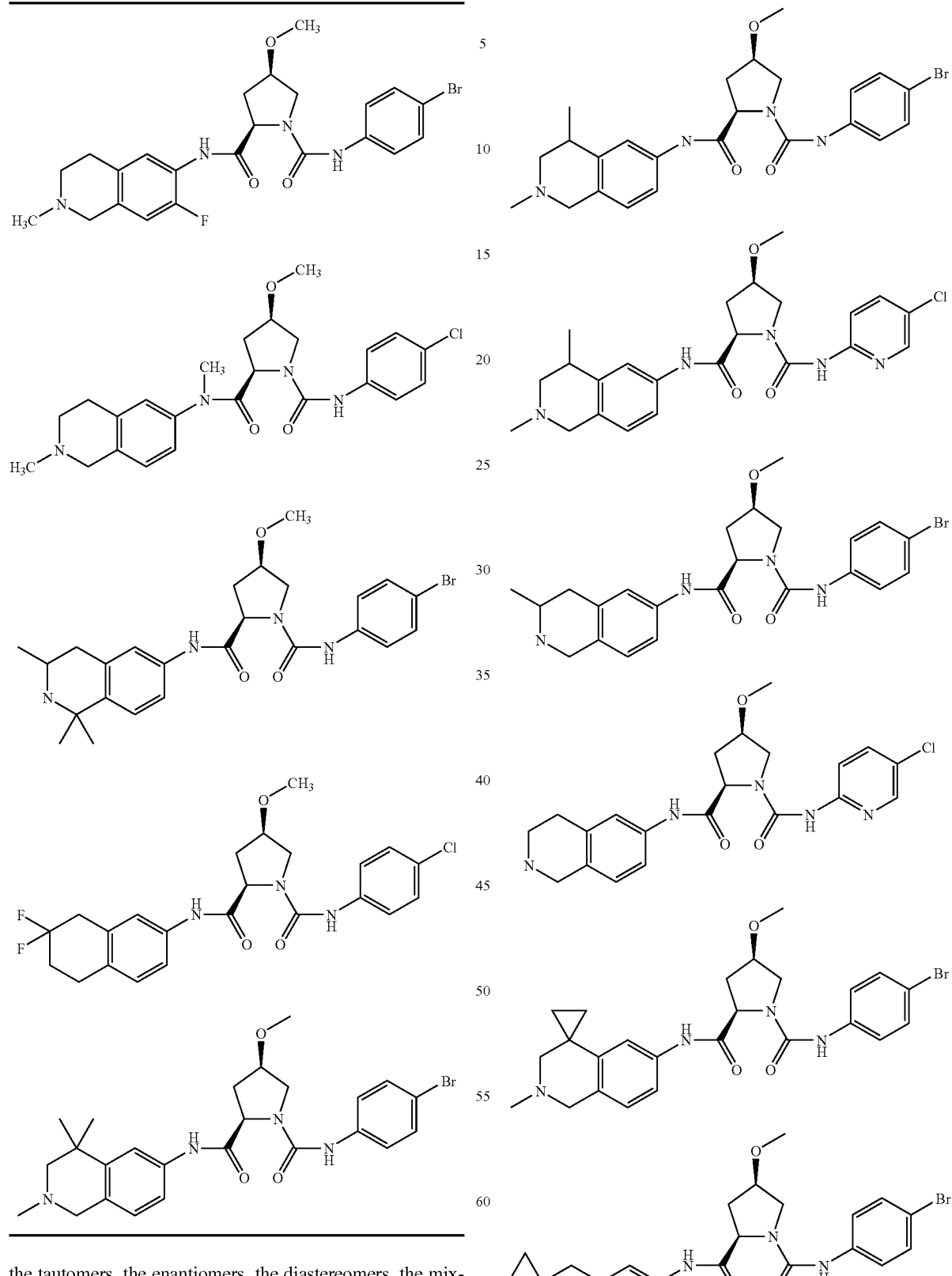
the tautomers, the enantiomers, the diastereomers, the mixtures and the salts thereof.
15. A compound according to claim 1, wherein said compound is selected from the group consisting of:

-continued
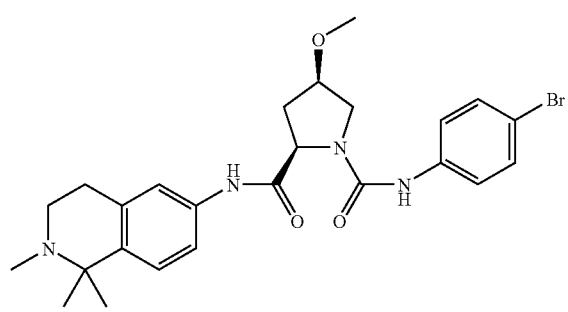
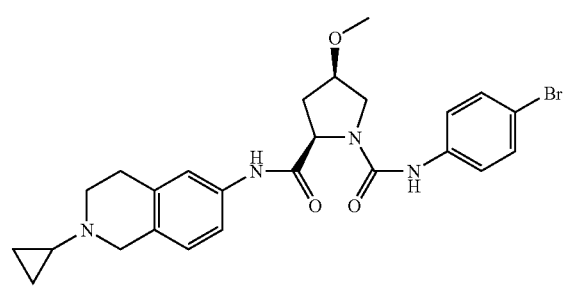
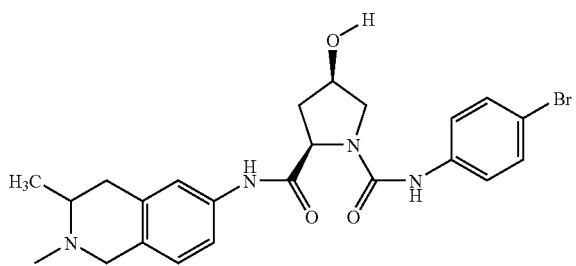
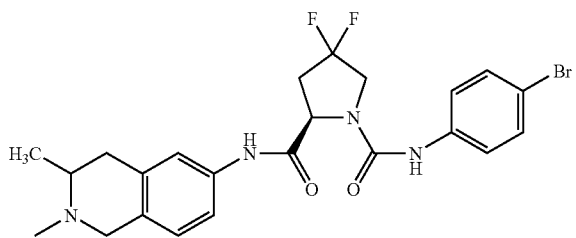
-continued
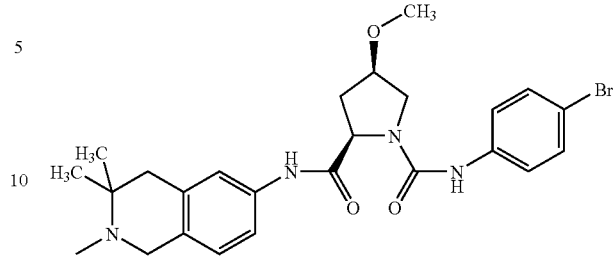
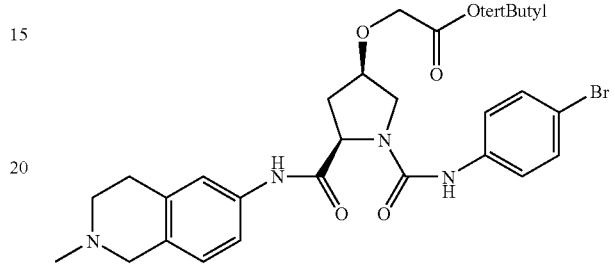
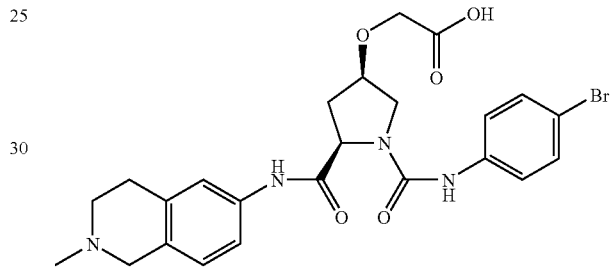
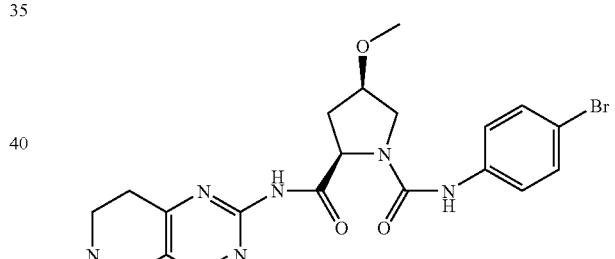
the tautomers, the enantiomers, the diastereomers, the mixtures and the salts thereof.
* * * * *